United States Patent
Cully et al.

(10) Patent No.: US 10,219,925 B2
(45) Date of Patent: Mar. 5, 2019

(54) CONTROLLED DEPLOYABLE MEDICAL DEVICE AND METHOD OF MAKING THE SAME

(71) Applicant: W. L. Gore & Associates, Inc., Newark, DE (US)

(72) Inventors: Edward H. Cully, Flagstaff, AZ (US); Keith M. Flury, Flagstaff, AZ (US); Michelle L. Gendron, Flagstaff, AZ (US); Stanislaw L. Zukowski, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 529 days.

(21) Appl. No.: 14/208,441

(22) Filed: Mar. 13, 2014

(65) Prior Publication Data
US 2014/0194968 A1    Jul. 10, 2014

Related U.S. Application Data

(63) Continuation of application No. 12/478,331, filed on Jun. 4, 2009, now abandoned.

(60) Provisional application No. 61/058,776, filed on Jun. 4, 2008.

(51) Int. Cl.
| | |
|---|---|
| *A61F 2/954* | (2013.01) |
| *A61F 2/06* | (2013.01) |
| *A61F 2/95* | (2013.01) |
| *A61F 2/07* | (2013.01) |

(52) U.S. Cl.
CPC ............ *A61F 2/954* (2013.01); *A61F 2/07* (2013.01); *A61F 2002/065* (2013.01); *A61F 2002/9505* (2013.01); *A61F 2002/9511* (2013.01); *A61F 2002/9534* (2013.01)

(58) Field of Classification Search
CPC ... A61F 2/95–2/954; A61F 2/962–2/97; A61F 2002/9505–2002/9534; A61F 2002/9665
USPC .............. 606/108; 623/1.11–1.12, 1.23, 1.35
See application file for complete search history.

(56) References Cited

U.S. PATENT DOCUMENTS

| | | | |
|---|---|---|---|
| 4,738,666 A | 4/1988 | Fuqua | |
| 5,035,706 A | 7/1991 | Giantureo et al. | |
| 5,387,235 A | 2/1995 | Chuter | |
| 5,405,378 A | 4/1995 | Strecker | |
| 5,464,449 A * | 11/1995 | Ryan ..................... | A61F 2/07 600/36 |
| 5,554,183 A | 9/1996 | Nazari | |
| 5,643,279 A | 7/1997 | Trotta | |
| 5,662,702 A | 9/1997 | Keranen | |
| 5,683,451 A | 11/1997 | Lenker et al. | |

(Continued)

FOREIGN PATENT DOCUMENTS

| | | |
|---|---|---|
| EP | 0664107 | 1/1995 |
| EP | 0956833 | 11/1999 |

(Continued)

*Primary Examiner* — Darwin Erezo
*Assistant Examiner* — Jonathan Hollm

(57) ABSTRACT

Controlled deployable medical devices that are retained inside a body passage and in one particular application to vascular devices used in repairing arterial dilations, e.g., aneurysms. Such devices can be adjusted during deployment, thereby allowing at least one of a longitudinal or radial re-positioning, resulting in precise alignment of the device to an implant target site.

28 Claims, 18 Drawing Sheets

(56) References Cited

U.S. PATENT DOCUMENTS

| | | | |
|---|---|---|---|
| 5,693,083 A * | 12/1997 | Baker | A61B 17/11 606/195 |
| 5,713,948 A | 2/1998 | Uflacker | |
| 5,776,186 A | 7/1998 | Uflacker | |
| 5,800,521 A | 9/1998 | Orth | |
| 5,824,055 A | 10/1998 | Spiridigliozzi et al. | |
| 5,843,158 A | 12/1998 | Lenker et al. | |
| 5,957,929 A | 9/1999 | Brennemen | |
| 6,019,785 A | 2/2000 | Strecker | |
| 6,042,605 A | 3/2000 | Martin et al. | |
| 6,051,001 A | 4/2000 | Borghi | |
| 6,168,616 B1 | 1/2001 | Brown, III | |
| 6,235,051 B1 | 5/2001 | Murphy | |
| 6,245,097 B1 | 6/2001 | Inoue | |
| 6,251,132 B1 | 6/2001 | Ravenscroft et al. | |
| 6,270,520 B1 | 8/2001 | Inoue | |
| 6,280,464 B1 | 8/2001 | Hayashi | |
| 6,287,315 B1 | 9/2001 | Wijeratne et al. | |
| 6,302,891 B1 | 10/2001 | Nadal | |
| 6,352,561 B1 | 3/2002 | Leopold et al. | |
| 6,361,637 B2 | 3/2002 | Martin et al. | |
| 6,371,979 B1 | 4/2002 | Beyar et al. | |
| 6,416,536 B1 | 7/2002 | Yee | |
| 6,520,986 B2 | 2/2003 | Martin et al. | |
| 6,533,811 B1 | 3/2003 | Ryan et al. | |
| 6,551,350 B1 | 4/2003 | Thornton et al. | |
| 6,558,396 B1 | 5/2003 | Inoue | |
| 6,565,597 B1 | 5/2003 | Fearnot et al. | |
| 6,656,212 B2 | 12/2003 | Ravenscroft et al. | |
| 6,676,692 B2 | 1/2004 | Rabkin et al. | |
| 6,723,116 B2 | 4/2004 | Taheri | |
| 6,733,521 B2 | 5/2004 | Chobotov et al. | |
| 6,740,111 B1 | 5/2004 | Lauterjung | |
| 6,776,791 B1 | 8/2004 | Stallings et al. | |
| 6,821,291 B2 | 11/2004 | Bolea et al. | |
| 6,837,901 B2 | 1/2005 | Rabkin et al. | |
| 6,852,116 B2 | 2/2005 | Leonhardt et al. | |
| 6,855,159 B1 | 2/2005 | Tanner et al. | |
| 6,916,335 B2 | 7/2005 | Kanji | |
| 6,945,990 B2 * | 9/2005 | Greenan | A61F 2/95 623/1.12 |
| 6,984,244 B2 | 1/2006 | Perez et al. | |
| 7,074,235 B1 | 7/2006 | Roy | |
| 7,226,473 B2 * | 6/2007 | Brar | A61B 17/12045 623/1.11 |
| 7,803,177 B2 | 9/2010 | Hartley et al. | |
| 7,993,383 B2 | 8/2011 | Hartley et al. | |
| 8,043,356 B2 | 10/2011 | Kolbel et al. | |
| 8,252,037 B2 | 8/2012 | Styrc et al. | |
| 8,361,137 B2 | 1/2013 | Perouse | |
| 8,845,709 B2 | 9/2014 | Styrc et al. | |
| 9,107,771 B2 | 8/2015 | Wubbeling et al. | |
| 9,198,787 B2 | 12/2015 | Kratzberg et al. | |
| 9,314,355 B2 | 4/2016 | Styrc et al. | |
| 9,375,308 B2 | 6/2016 | Norris | |
| 9,427,317 B2 | 8/2016 | Styrc | |
| 2002/0038144 A1 | 3/2002 | Trout et al. | |
| 2002/0099431 A1 | 7/2002 | Armstrong et al. | |
| 2002/0161377 A1 | 10/2002 | Rabkin | |
| 2002/0161427 A1 | 10/2002 | Rabkin et al. | |
| 2002/0188344 A1 | 12/2002 | Bolea et al. | |
| 2003/0004560 A1 | 1/2003 | Chobotov et al. | |
| 2003/0135257 A1 * | 7/2003 | Taheri | A61B 17/00234 623/1.11 |
| 2003/0135269 A1 | 7/2003 | Swanstrom | |
| 2003/0199966 A1 | 10/2003 | Shiu et al. | |
| 2003/0225446 A1 | 12/2003 | Hartley | |
| 2004/0260383 A1 | 4/2004 | Honda et al. | |
| 2004/0087965 A1 | 5/2004 | Levine et al. | |
| 2004/0093058 A1 | 5/2004 | Cottone et al. | |
| 2004/0093063 A1 | 5/2004 | Wright et al. | |
| 2004/0138734 A1 | 7/2004 | Chobotov et al. | |
| 2004/0143316 A1 | 7/2004 | Spiridigliozzi et al. | |
| 2004/0147939 A1 | 7/2004 | Rabkin et al. | |
| 2004/0210298 A1 | 10/2004 | Rabkin et al. | |
| 2004/0220655 A1 | 11/2004 | Swanson et al. | |
| 2004/0230287 A1 | 11/2004 | Hartley et al. | |
| 2005/0038495 A1 | 2/2005 | Greenan | |
| 2005/0060018 A1 | 3/2005 | Ditman | |
| 2005/0085890 A1 | 4/2005 | Rassmussen et al. | |
| 2005/0090834 A1 | 4/2005 | Chiang et al. | |
| 2005/0107862 A1 | 5/2005 | Ohlenschlaeger | |
| 2005/0119722 A1 * | 6/2005 | Styrc | A61F 2/95 623/1.12 |
| 2005/0182290 A1 | 8/2005 | Lau et al. | |
| 2005/0182476 A1 | 8/2005 | Hartley et al. | |
| 2006/0004433 A1 | 1/2006 | Greenberg et al. | |
| 2006/0036314 A1 | 2/2006 | Perez et al. | |
| 2006/0155363 A1 * | 7/2006 | LaDuca | A61F 2/856 623/1.16 |
| 2006/0184226 A1 | 8/2006 | Austin | |
| 2006/0190075 A1 | 8/2006 | Jordan et al. | |
| 2006/0229699 A1 | 10/2006 | Tehrani | |
| 2006/0259119 A1 | 11/2006 | Rucker | |
| 2006/0259122 A1 | 11/2006 | Eliseev | |
| 2006/0276872 A1 | 12/2006 | Arbefeuille et al. | |
| 2007/0010875 A1 | 1/2007 | Trout et al. | |
| 2007/0016281 A1 | 1/2007 | Melsheimer | |
| 2007/0043425 A1 | 1/2007 | Hartley et al. | |
| 2007/0043432 A1 | 1/2007 | Christensen et al. | |
| 2007/0088424 A1 | 4/2007 | Greenberg et al. | |
| 2007/0100427 A1 * | 5/2007 | Perouse | A61F 2/07 623/1.11 |
| 2007/0142894 A1 | 6/2007 | Moore et al. | |
| 2007/0225797 A1 | 9/2007 | Krivoruhko | |
| 2007/0233223 A1 * | 10/2007 | Styrc | A61F 2/2439 623/1.11 |
| 2008/0082154 A1 | 4/2008 | Tseng et al. | |
| 2014/0330368 A1 | 11/2014 | Gloss et al. | |

FOREIGN PATENT DOCUMENTS

| | | |
|---|---|---|
| EP | 1842508 | 10/2007 |
| EP | 1923024 | 5/2008 |
| FR | 2 896 405 | 1/2006 |
| JP | 2005-179587 | 5/2005 |
| JP | 2005-537107 | 12/2005 |
| JP | 2008-119481 | 5/2008 |
| WO | WO1995/001761 | 1/1995 |
| WO | WO1997/003624 | 2/1997 |
| WO | WO2001060285 | 8/2001 |
| WO | 2004/021932 | 3/2004 |
| WO | WO-2005/079705 | 9/2005 |
| WO | WO2006/134258 | 12/2006 |
| WO | WO2007/025101 | 3/2007 |
| WO | 2008/029296 | 3/2008 |
| WO | WO2008/042266 | 4/2008 |

* cited by examiner

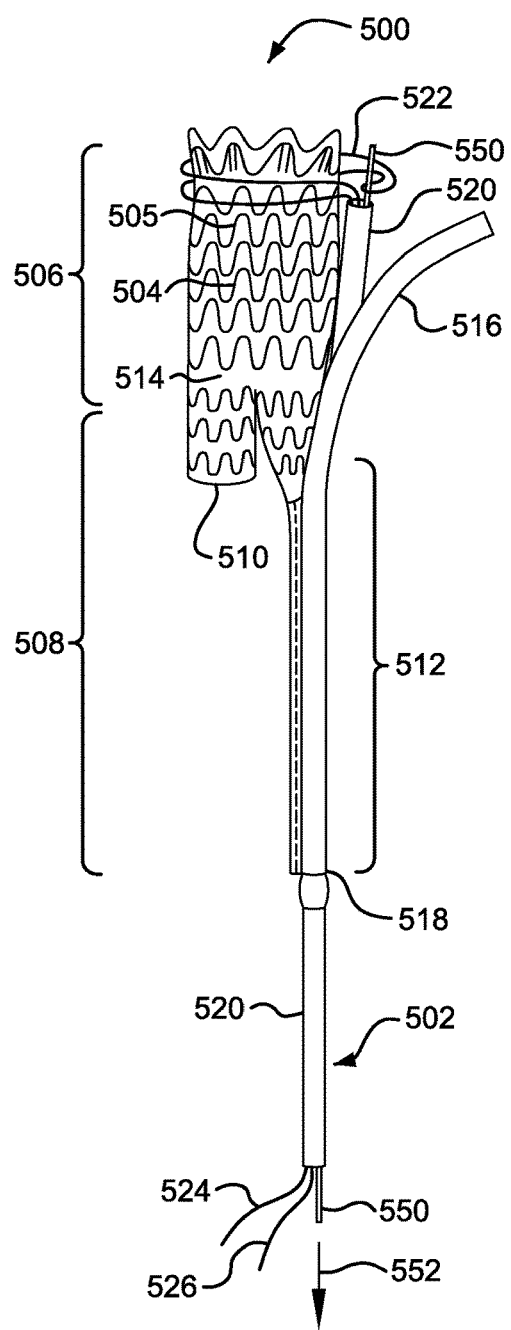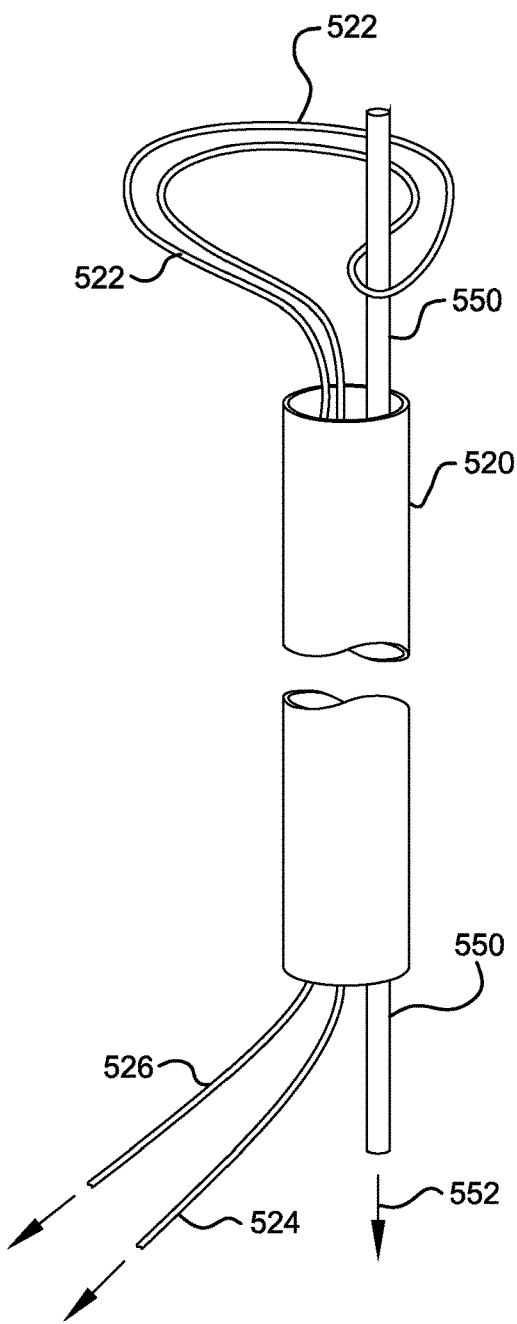
FIG. 5A
FIG. 5B

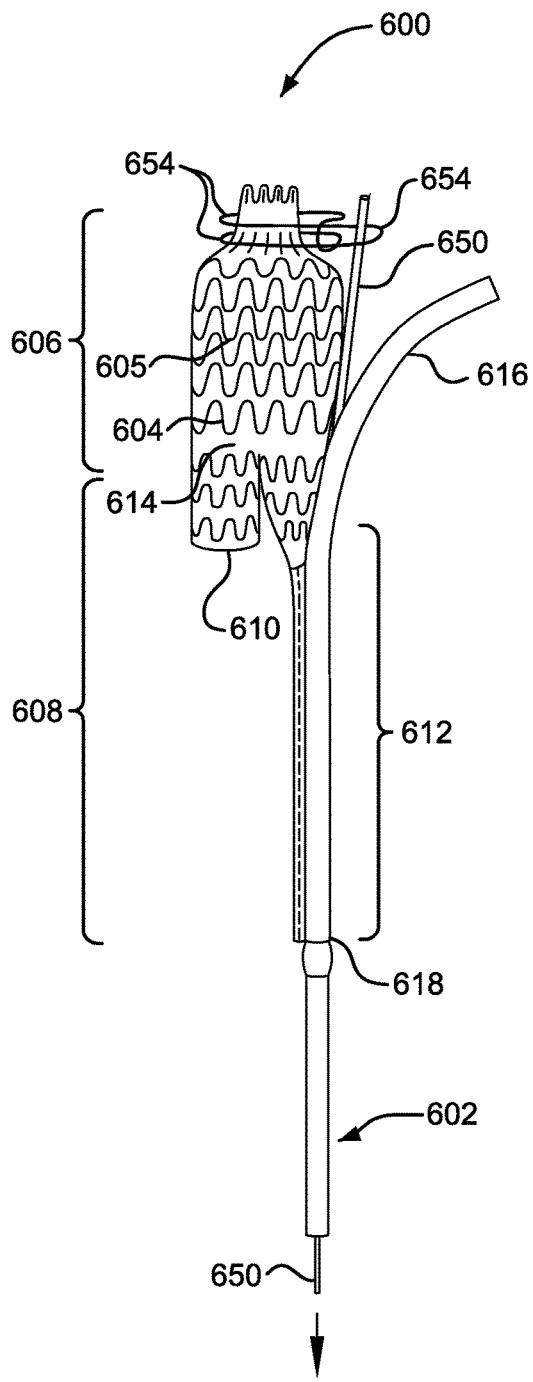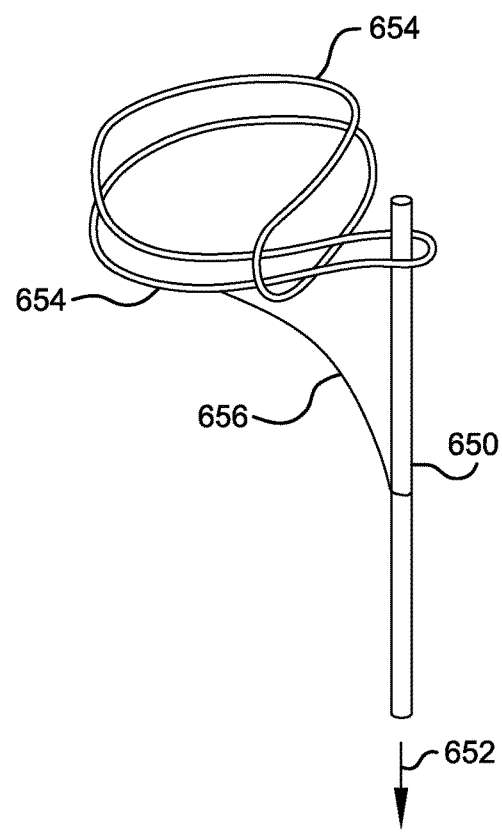
FIG. 6A
FIG. 6B

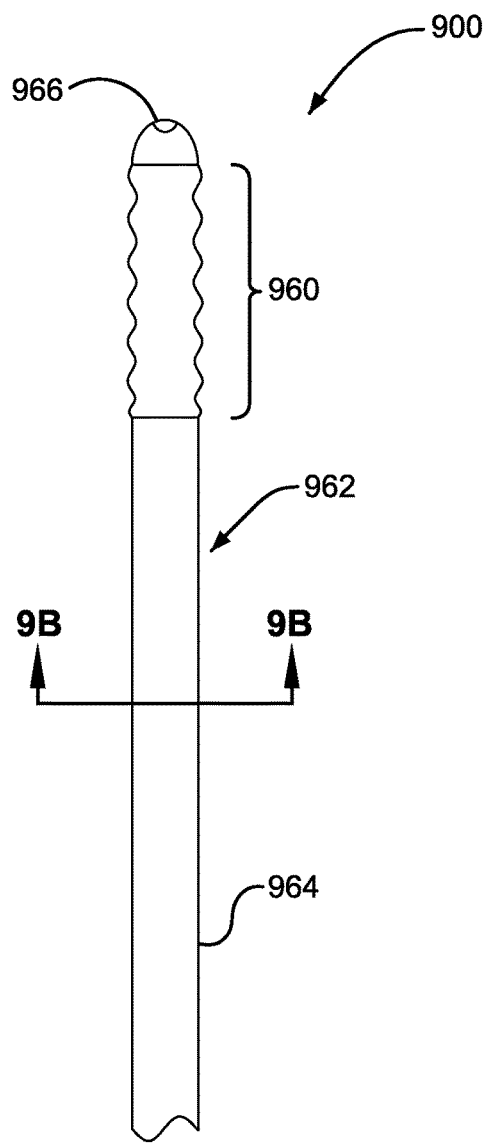
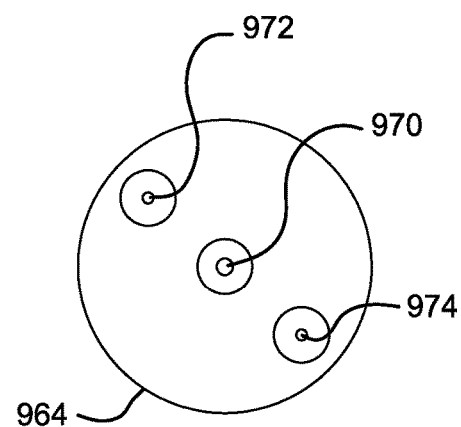
FIG. 9A
FIG. 9B

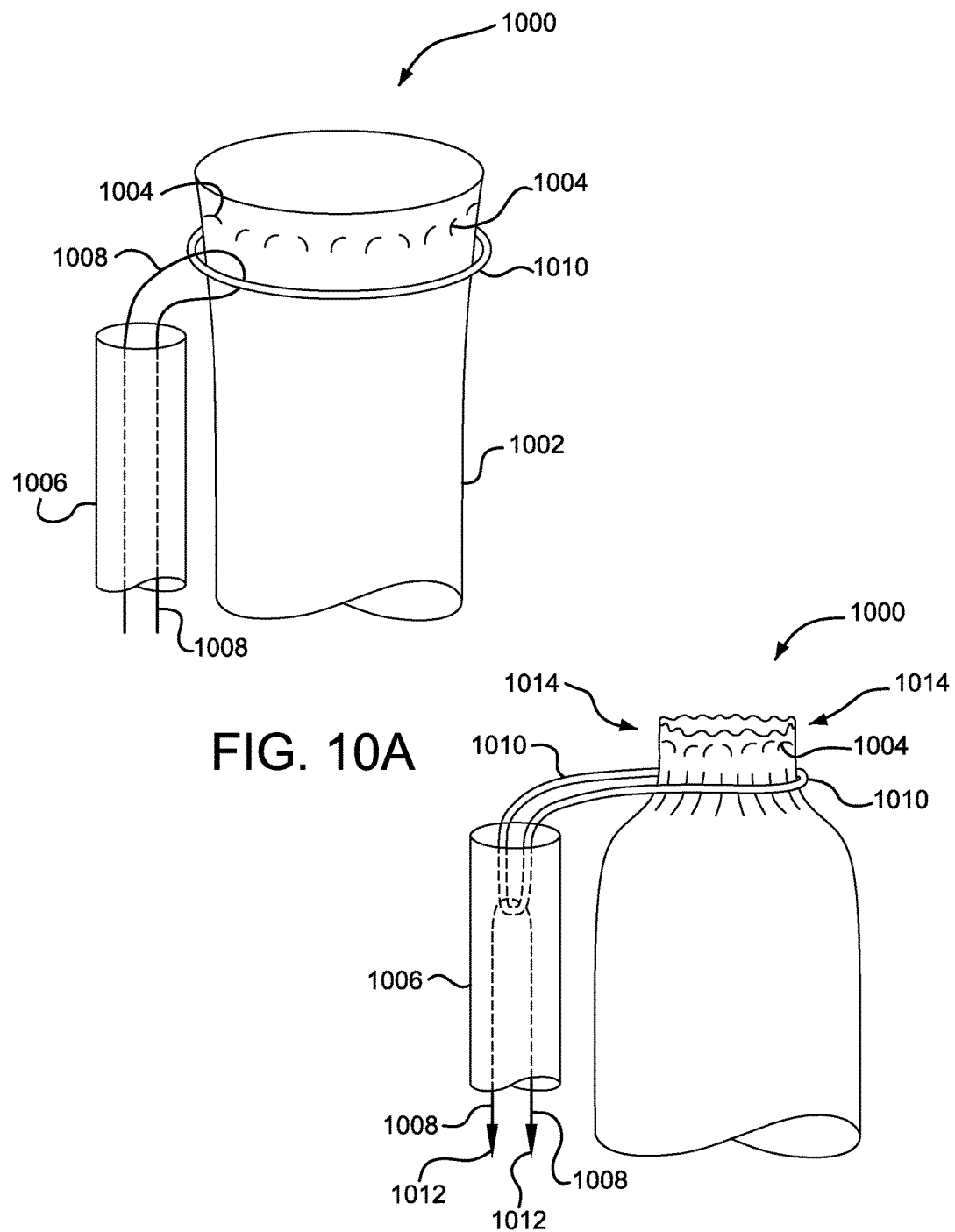

CONTROLLED DEPLOYABLE MEDICAL DEVICE AND METHOD OF MAKING THE SAME

BACKGROUND OF THE INVENTION

Field of the Invention

The invention relates generally to devices that are retained inside a body passage and in one particular application to vascular devices used in repairing arterial dilations, e.g., aneurysms. More particularly, the invention is directed toward devices that can be adjusted during deployment, thereby allowing at least one of a longitudinal or radial re-positioning of the device prior to final placement of the device.

Discussion of the Related Art

The invention will be discussed generally with respect to deployment of a bifurcated stent graft into the abdominal aorta but is not so limited and may apply to device deployment into other body lumens. When delivering a stent graft by intraluminal or endovascular methods, it is important to know the precise location of the device in the vasculature. Controlling this precise location is particularly important when the device is intended to be deployed in close proximity to branch vessels or adjacent to weakened portions of the aortic wall. Typical stent grafts used to repair an aortic aneurysm incorporate a proximal (i.e. portion of the stent graft closest to the heart) anchoring system intended to limit longitudinal displacement of the stent graft. Often this anchoring system must be precisely placed to avoid occlusion of a branch vessel or to avoid placement within a compromised and damaged portion of the aortic wall.

An improved delivery system for such stent grafts would include a means for allowing precise longitudinal and rotational placement of the stent graft and anchoring system. The precise position of the stent graft and anchoring system would be adjusted and visualized prior to full deployment of the device. Ideally the delivery system would allow the device to be repositioned if the prior deployment position was undesirable.

BRIEF DESCRIPTION OF THE DRAWINGS

The accompanying drawings are included to provide a further understanding of the invention and illustrate certain aspects of the invention.

In the drawings:

FIG. 5A is a medical apparatus according to an embodiment of the invention.

FIG. 5B is an enlarged simplified view of a medical apparatus according to an embodiment of the invention.

FIG. 6A is a medical apparatus according to an embodiment of the invention.

FIG. 6B is an enlarged simplified view of a medical apparatus according to an embodiment of the invention.

FIG. 9A is an apparatus according to an embodiment of the invention.

FIG. 9B is a cross-sectional view of FIG. 9A along line A to A'.

FIGS. 10A-10H illustrates a deployment procedure of an apparatus according to FIGS. 2A-2B.

DETAILED DESCRIPTION

Figures 1A, 1B:
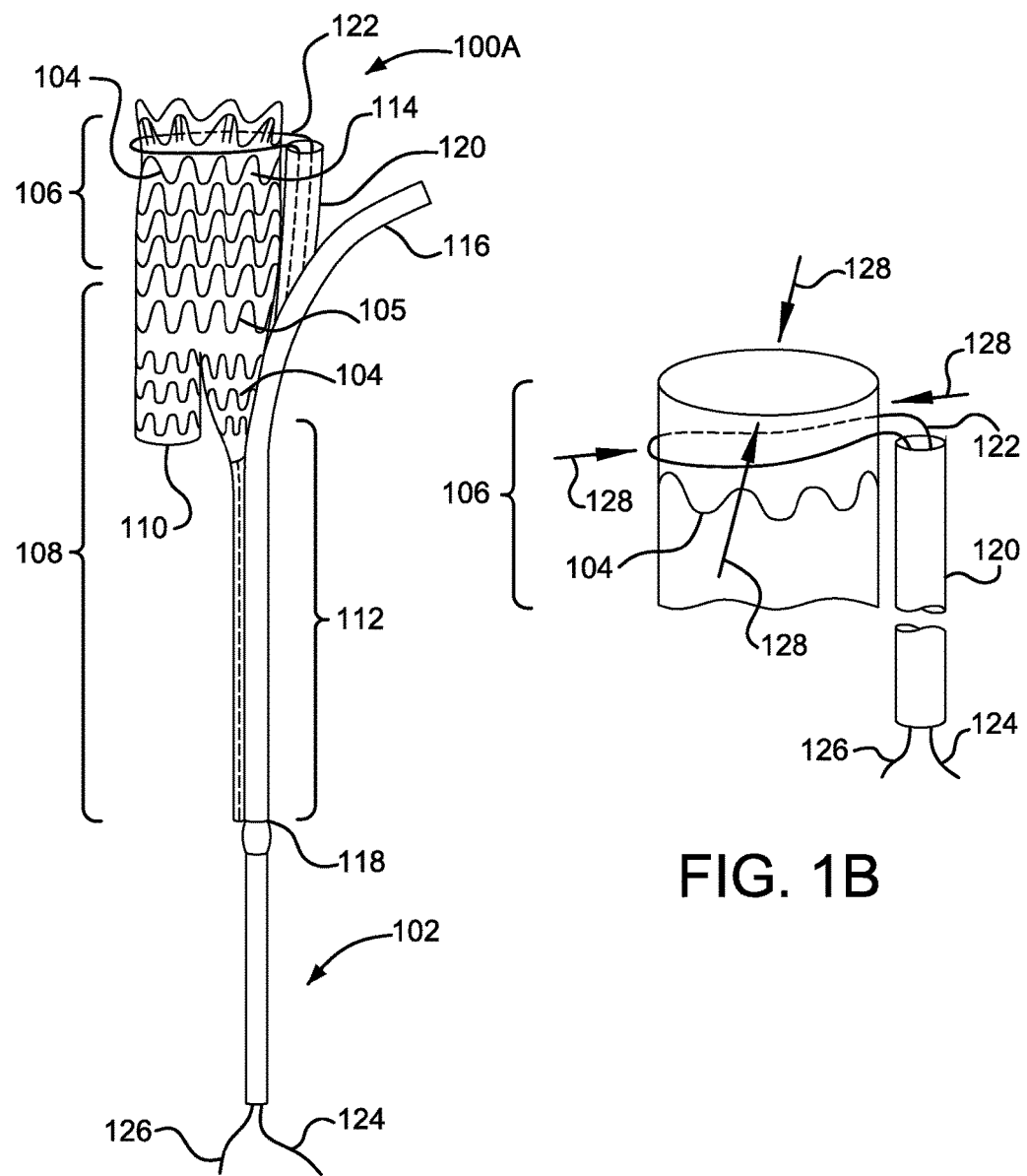
FIG. 1A is a medical apparatus according to an embodiment of the invention.
FIG. 1B is an enlarged simplified view of the medical apparatus according to an embodiment of the invention.

The invention relates generally to a novel medical apparatus that includes a device capable of being retained inside a body passage and in one particular application to vascular devices. More particularly, the invention is directed toward devices that can be adjusted during deployment, thereby allowing at least one of a longitudinal or radial re-positioning of the device.

In an embodiment of the invention, the medical apparatus includes a catheter assembly having a proximal end portion and distal end portion. A hub can optionally be arranged on the distal end portion of the catheter assembly. A stent is arranged on the proximal end portion of the catheter. The stent has an inner surface and an outer surface. The stent can be any suitable configuration. In one embodiment, the stent is configured from multiple turns of an undulating element. A graft member can be arranged about at least a portion of the stent. The stent may be self-expandable, balloon-expandable or a combination of self-expandable and balloon-expandable.

A tube extends from the proximal end portion to the distal end portion of the catheter. A first movable element, having a first and second end, is arranged around the outer surface of the stent. The first and second end of the first movable element are capable of extending out the distal end portion of the tube and the first movable element is capable of radially compressing at least a portion of the stent.

Optionally, a second movable element can be in communication with the first movable element, wherein the second movable element is arranged around the outer surface of stent and the first movable element is looped over the second movable element. A sheath material can cover at least a portion of the stent, wherein the sheath material is capable of holding the stent at a first diameter. A filament can surround the stent and a pin can extend from the tube and is capable of holding the filament surrounding the stent at a second diameter which is greater than the first diameter. The pin extending from the tube is capable of releasing the filament surrounding the stent to a third diameter which is greater than the second diameter.

In some embodiments, the stents can be used to at least fix the medical apparatus inside a portion of patient's anatomy. The stent can be constructed from materials that are flexible and strong. The stent can be formed from, for example, degradable bioabsorable materials, biodigestible materials, polymeric materials, metallic materials and combinations thereof. In addition, these materials may be reinforced and/or coated with other materials, such as polymeric materials and the like. The coating may be chosen to reduce acidic or basic effects of the gastrointestinal tract, e.g., with a thermoplastic coating such as ePTFE and the like.

The stents can be fabricated using any suitable methods and materials. For example, stents can be fabricated according to the teachings as generally disclosed in U.S. Pat. No. 6,042,605 issued to Martin, et al., U.S. Pat. No. 6,361,637 issued to Martin, et al. and U.S. Pat. No. 6,520,986 issued to Martin, et al. For example, stents can have various configurations as known in the art and can be fabricated, for example, from cut tubes, wound wires (or ribbons), flat patterned sheets rolled into a tubular form, combinations thereof, and the like. Stents can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicone polymers; metals such as stainless steels, cobalt-chromium alloys and nitinol and biologically derived materials such as bovine arteries/veins, pericardium and collagen. Stents can also comprise bioresorbable materials such as poly(amino acids), poly(anhydrides), poly(caprolactones), poly(lactic/glycolic acid) polymers, poly(hydroxybutyrates) and poly(orthoesters).

The stents can be formed into a variety of different geometric configurations having constant and/or varied thickness as known in the art. The geometric configurations may include many conventional stent configurations such as a helically wrapped stent, z-shape stent, tapered stent, coil stent, combinations thereof, and the like. The stents can be formed in a variety of patterns, such as, a helix pattern, ring pattern, combinations thereof, and the like.

Grafts can have various configurations as known in the art and can be fabricated, for example, from tubes, sheets or films formed into tubular shapes, woven or knitted fibers or ribbons or combinations thereof. Graft materials can include, for example, conventional medical grade materials such as nylon, polyester, polyethylene, polypropylene, polytetrafluoroethylene, polyvinylchloride, polyurethane and elastomeric organosilicone polymers.

Stents can be used alone or in combination with graft materials. Stents can be configured on the external or internal surface of a graft or may be incorporated into the internal wall structure of a graft. Stent or stent grafts can be delivered endoluminally by various catheter based procedures known in the art. For example self-expanding endoluminal devices can be compressed and maintained in a constrained state by an external sheath. The sheath can be folded to form a tube positioned external to the compressed device. The sheath edges can be sewn together with a deployment cord that forms a "chain stitch". To release and deploy the constrained device, one end of the deployment cord can be pulled to disrupt the chain stitch, allowing the sheath edges to separate and release the constrained device. Constraining sheaths and deployment cord stitching can be configured to release a self-expanding device in several ways. For example a constraining sheath may release a device starting from the proximal device end, terminating at the distal device end. In other configurations the device may be released starting from the distal end. Self expanding devices may also be released from the device center as the sheath disrupts toward the device distal and proximal ends.

Details relating to constraining sheath materials, sheath methods of manufacture and stent graft compression techniques can be found in, for example, U.S. Pat. No. 6,352,561 issued to Leopold, et al., and U.S. Pat. No. 6,551,350 issued to Thornton, et al.

The catheter and hub assemblies can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyether block amide or thermoplastic copolyether, polyvinylchloride, polyurethane, elastomeric organosilicone polymers, and metals such as stainless steels and nitinol.

Turning to the figures, FIG. 1A is a medical apparatus according to an embodiment of the invention. FIG. 1B is an enlarged simplified view of a portion of the medical apparatus shown in FIG. 1A.

Referring to FIGS. 1A and 1B, the medical apparatus is generally depicted as reference numeral 100A. The medical apparatus 100A includes catheter assembly 102, stent 104 arranged on the proximal end portion of the catheter assembly 102. The stent 104 has an inner surface, an outer surface, and in this embodiment is configured from multiple turns of an undulating element 105. The undulating element 105 can be configured, for example, in a ring or helical pattern.

The stent 104 has a proximal end portion 106 and distal end portion 108. The distal end portion 108 is formed into a branch having a first leg 110 and a second leg 112.

A graft member 114 is arranged about the stent 104.

The stent 104 and graft member 114 are constrained into a compacted delivery state by a first sheath 116 and second sheath 118. As shown in FIG. 1A, the first sheath 116 has been released, allowing at least a portion of the stent 104 to expand as shown. The second sheath 118 is coupling the second leg 112 to the catheter assembly 102 as shown.

A tube 120 extends from a proximal end portion to a distal end portion of the catheter assembly 102. In the figure, the tube 120 is positioned adjacent the outer surface of the stent 104 and graft 114. The tube 120 is attached to the catheter assembly 102 and not attached to the stent 104 or graft 114. A movable element 122 (e.g., a fiber cord, string, wire, etc.) having a first end 124 and second end 126 surrounds the stent 104 and graft member 114. The first end 124 and second end 126 of the movable element 122 extend out a distal end portion of the tube 120. For example, the movable element 122 is threaded through the tube from a distal end to a proximal end and is looped around the proximal end portion 106 of the stent 104 and graft member 114. As shown in FIG. 1B, by pulling the first end 124 and the second end 126 in a distal direction the movable element 122 is capable of radially compressing at least a portion of the stent 104 as indicated by arrows 128.

Figure 1C:
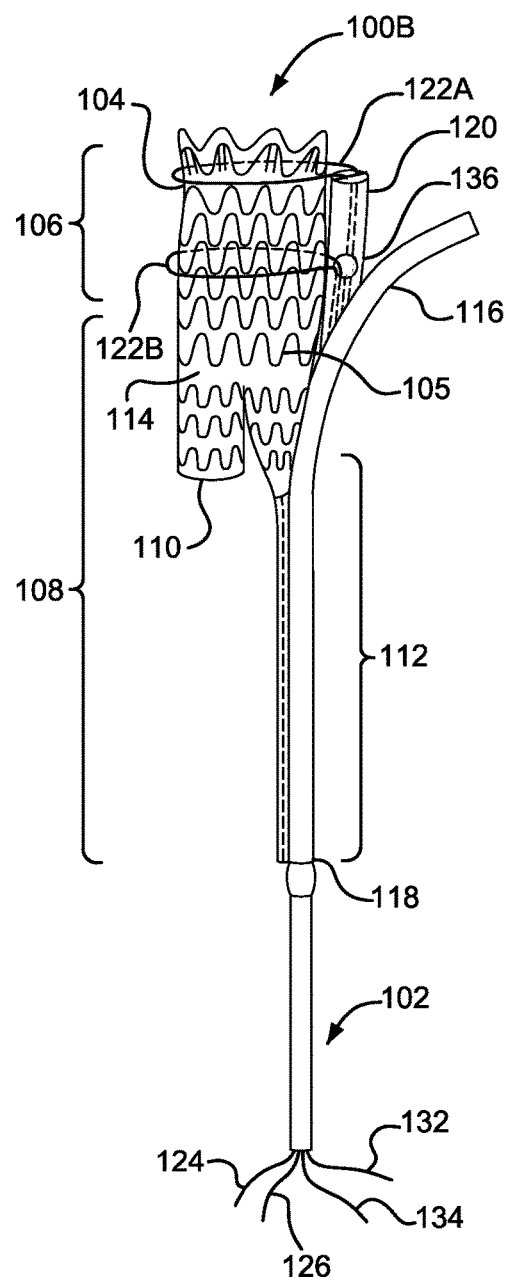
FIG. 1C is a medical apparatus according to an embodiment of the invention.
Figure 1D:
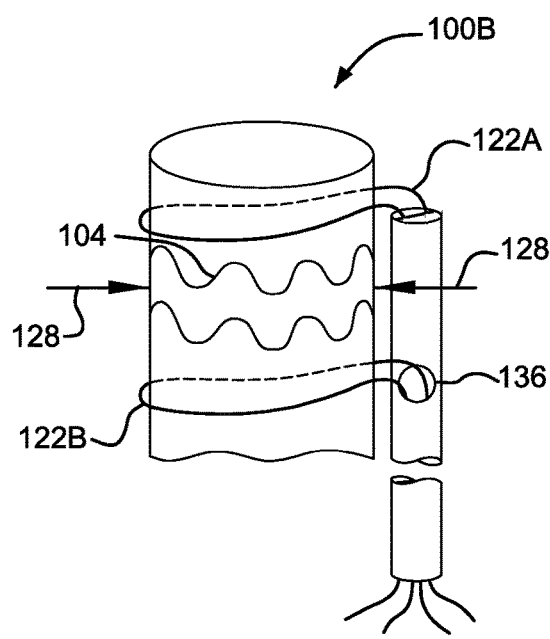
FIG. 1D is an enlarged simplified view of the medical apparatus according to a second embodiment of the invention.

FIG. 1C is a medical apparatus according to an embodiment of the invention. FIG. 1D is an enlarged simplified view of a portion of the medical apparatus shown as FIG. 1C.

Referring to FIGS. 1C and 1D, the medical apparatus is generally depicted as reference numeral 100B. The medical apparatus of FIGS. 1C and 1D is similar to the medical apparatus as shown in FIGS. 1A and 1B. The medical apparatus includes catheter assembly 102, stent 104 arranged on the proximal end portion of catheter assembly 102. Stent 104 has an inner surface, an outer surface, and is configured from multiple turns of an undulating element 105. The undulating element 105 may be configured, for example, in a ring or helical pattern.

The stent 104 has a proximal end portion 106 and distal end portion 108. The distal end portion 108 is formed into a branch having a first leg 110 and a second leg 112.

A graft member 114 is arranged about the stent 104.

The stent 104 and graft member 114 are constrained into a compacted delivery state by a first sheath 116 and second sheath 118. As shown in FIG. 1C, the first sheath 116 has been released allowing at least a portion of the stent to expand as shown. The second sheath 118 is coupling the second leg 112 to the catheter assembly 102 as shown.

A tube 120 extends from a proximal end portion to a distal end portion of the catheter assembly 102. The tube 120 is positioned adjacent the outer surface of the stent 104 and graft 114. The tube 120 is attached to the catheter assembly 102 and not attached to the stent 104 or graft 114. A movable element 122A having a first end 124 and second end 126 surrounds the stent 104 and graft member 114. The first end 124 and second end 126 of the movable element 122A extend out a distal end portion of the tube 120. For example, the movable element 122A is threaded through the tube from a distal end to a proximal end and is looped around the proximal end portion 106 of the stent 104 and graft member 114.

Moreover, an additional movable element 122B having first end 132 and second end 134 surrounds the stent 104 and graft member 114. The first end 132 and second end 134 of the additional movable element 122B extend out a distal end portion of the tube 120. The additional movable element 122B is threaded through the tube from a distal end to an intermediate opening 136 in the tube 120 and is looped around an intermediate portion of the stent 104 and graft member 114. As shown in FIG. 1D, by pulling the ends of the moveable elements in a distal direction the movable element 122A and the additional movable element 122B are capable of radially compressing at least a portion of the stent 104 as indicated by arrows 128. It should be understood that additional moveable elements can be provided.

Figures 2A, 2B:
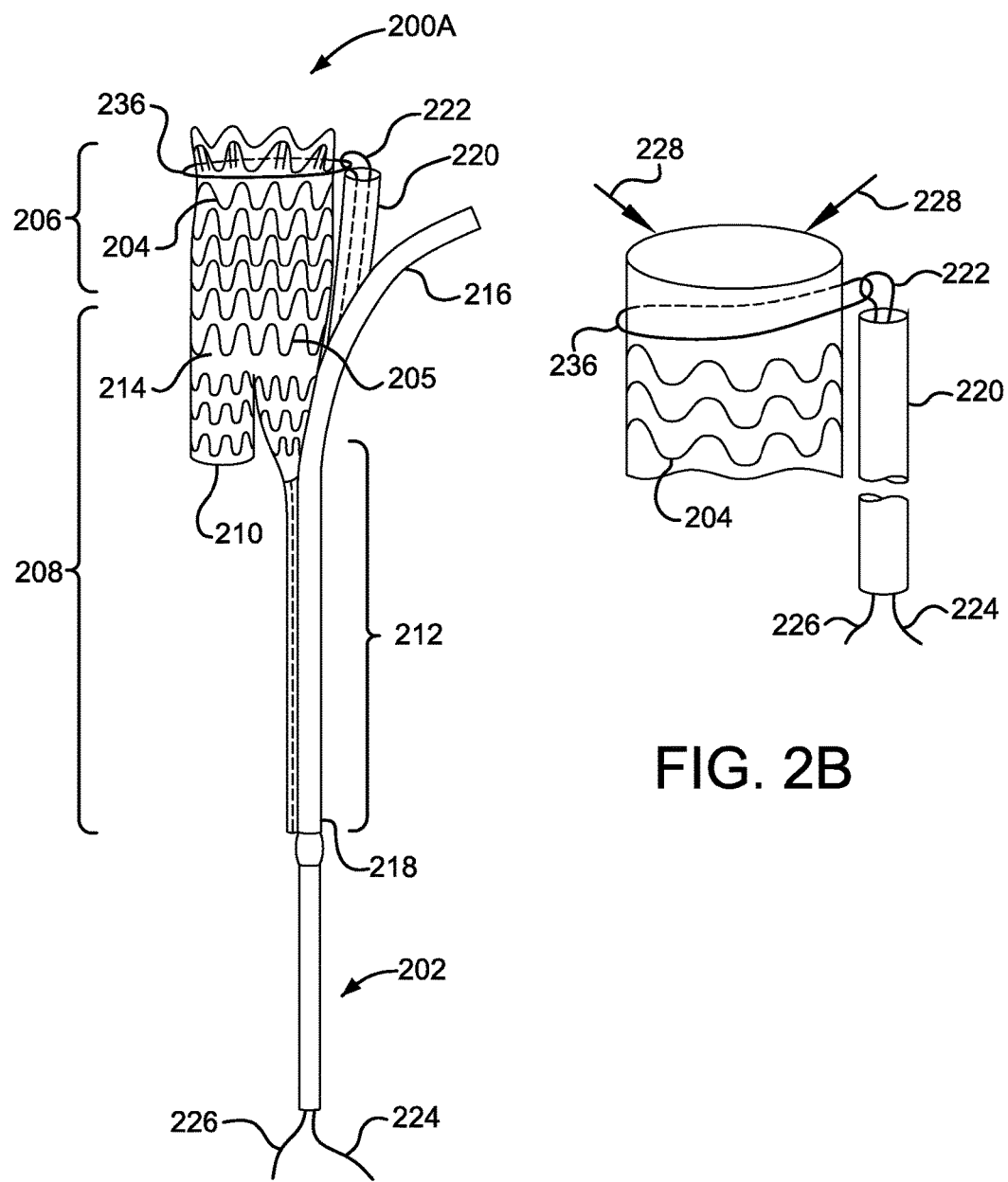
FIG. 2A is a medical apparatus according to an embodiment of the invention.
FIG. 2B is an enlarged simplified view of a medical apparatus according to an embodiment of the invention.

FIG. 2A is a medical apparatus according to an embodiment of the invention, shown in a partially deployed state. FIG. 2B is an enlarged simplified view of a portion of the medical apparatus shown in FIG. 2A.

Referring to FIGS. 2A and 2B, the medical apparatus is generally depicted by reference numeral 200A. The medical apparatus 200A includes a catheter assembly 202, and stent 204 arranged on the proximal end portion of the catheter assembly 202. The stent 204 has an inner surface, an outer surface, and is configured from multiple turns of an undulating element 205. The undulating element 205 can be configured, for example, in a ring or helical pattern.

The stent 204 has a proximal end portion 206 and distal end portion 208. The distal end portion 208 is formed into a branch having a first leg 210 and a second leg 212.

A graft member 214 is arranged about the stent 204.

The stent 204 and graft member 214 are constrained into a compacted delivery state by a first sheath 216 and second sheath 218. As shown in FIG. 2A, the first sheath 216 has been released allowing at least a portion of the stent to expand. The second sheath 218 is coupling the second leg 212 to the catheter assembly 202 as shown.

A tube 220 extends from a proximal end portion to a distal end portion of the catheter assembly 202. In this embodiment, the tube 220 is positioned adjacent the outer surface of the stent 204 and graft 214. In this embodiment, the tube 220 is attached to the catheter assembly 202 and not attached to the stent 204 or graft 214.

A second movable element 236 is in communication with a first movable element 222. The second movable element 236 surrounds the stent 204 and the first movable element 222 is looped through the second movable element 236.

The first end 224 and second end 226 of the first movable element 222 extend out a distal end portion of the tube 220. For example, the first movable element 222 is threaded through the tube from a distal end to a proximal end and is looped through the second movable element 236.

As shown in FIG. 2B, when the two ends 224 and 226 of the first movable element are pulled in a distal direction, the movable element 222 pulls on the second movable element 236, radially compressing at least a portion of the stent 204 as indicated by arrows 228.

Figures 2C, 2D:
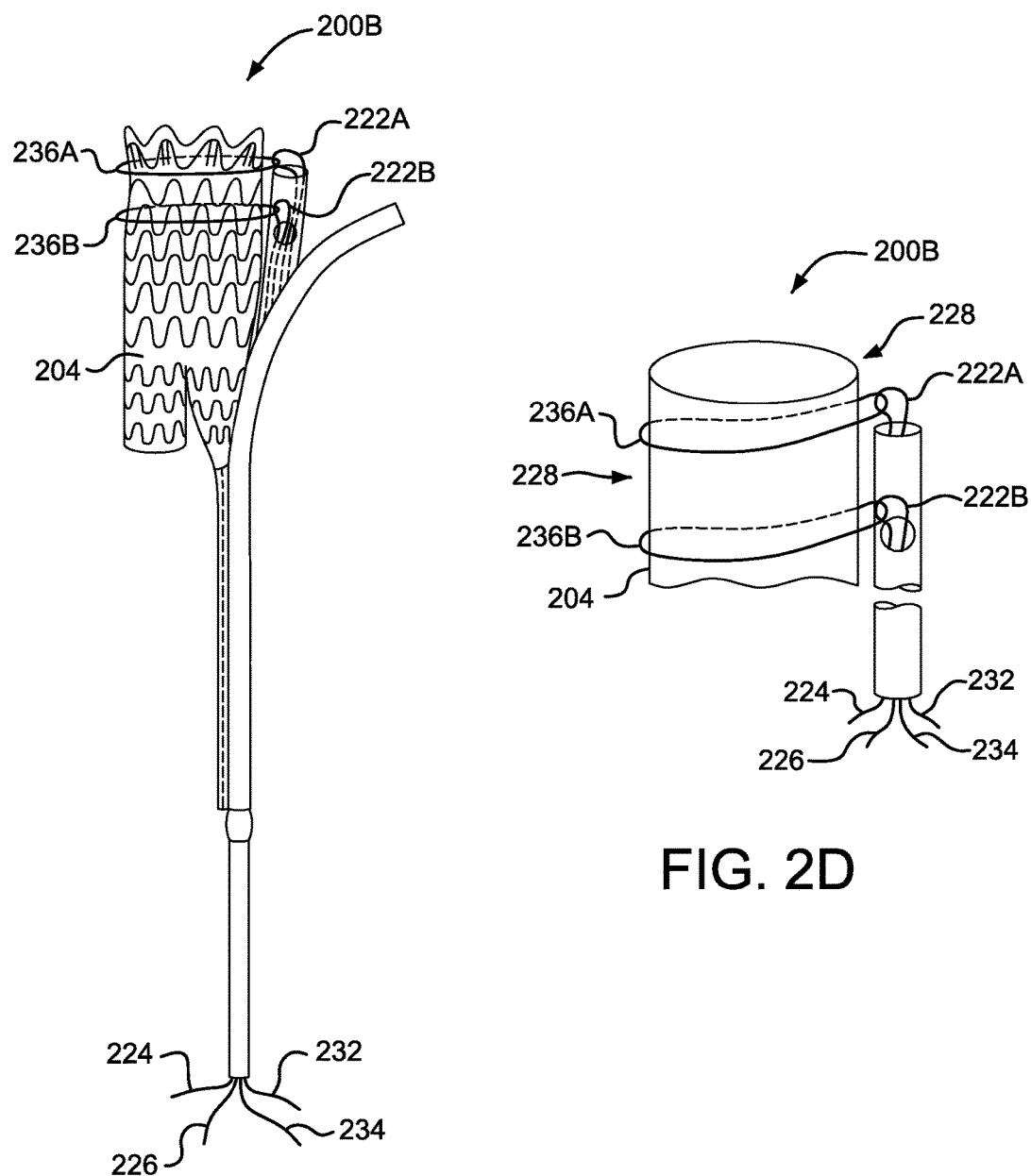
FIG. 2C is a medical apparatus according to an embodiment of the invention.
FIG. 2D is an enlarged simplified view of a medical apparatus according to an embodiment of the invention.

FIG. 2C is a medical apparatus according to an embodiment of the invention. FIG. 2D is an enlarged simplified view of a portion of the medical apparatus shown in FIG. 2C.

Referring to FIGS. 2C and 2D, the medical apparatus is generally depicted by reference numeral 200B. The medical apparatus of FIGS. 2C and 2D is similar to the medical apparatus as shown in FIGS. 2A and 2B.

Shown in FIGS. 2C and 2D, a second movable element 236A is in communication with a first movable element 222A. The second movable element 236A surrounds the stent 204 and the first movable element 222A is looped through the second movable element 236A.

An additional first movable element 222B along with an additional second movable element 236B are incorporated into the medical apparatus 200B.

As shown in FIG. 2D, when tension is applied to the two ends 224 and 226 of the first movable element 222A, the first movable element 222A pulls on the second movable element 236A, radially compressing at least a portion of the stent 204 as indicated by arrows 228. Similarly, when tension is applied to the two ends 232 and 234 of the additional first movable element 222B, the additional first movable element 222B pulls on the additional second movable element 236B, radially compressing at least a portion of the stent 204 as indicated by arrows 228.

Figure 3A:
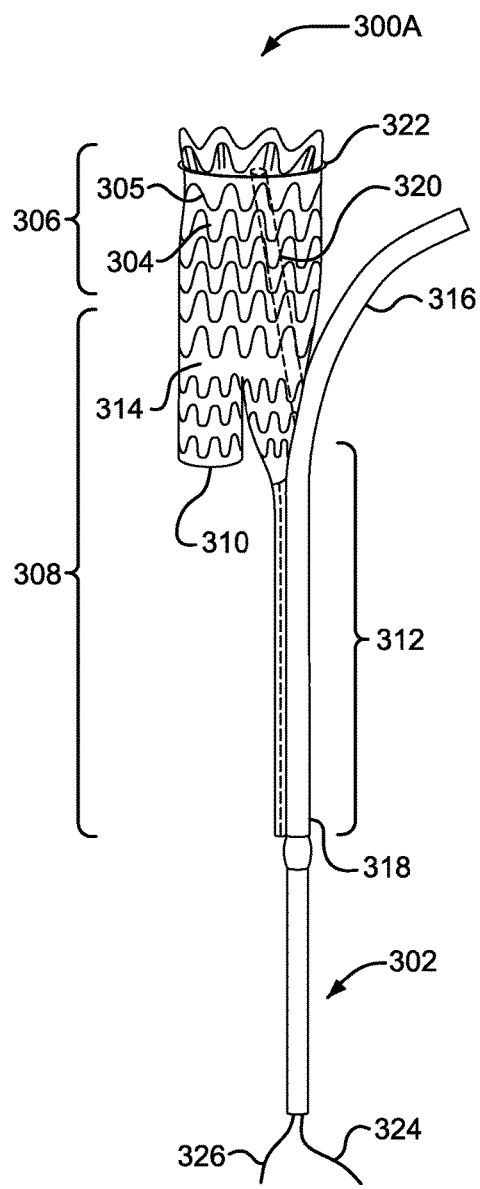
FIG. 3A is a medical apparatus according to an embodiment of the invention.
Figure 3B:
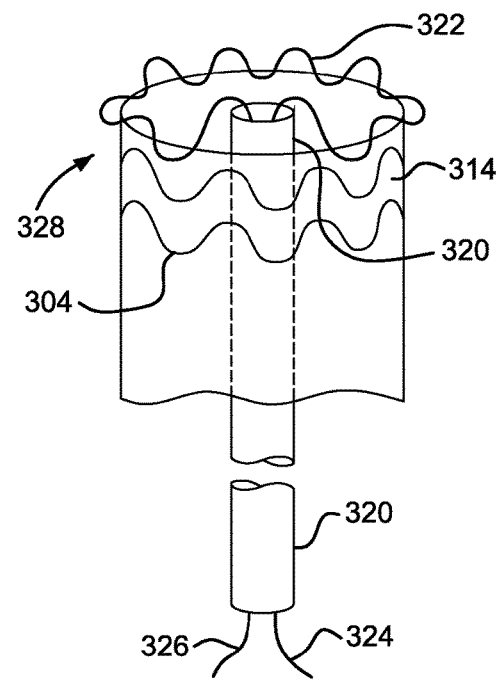
FIG. 3B is an enlarged simplified view of a medical apparatus according to an embodiment of the invention.

FIG. 3A is a medical apparatus according to an aspect of the invention. FIG. 3B is an enlarged simplified view of a portion of the medical apparatus shown in FIG. 3A.

Referring to FIGS. 3A and 3B, the medical apparatus is generally depicted by reference numeral 300A. The medical apparatus 300A includes a catheter assembly 302, and stent 304 arranged on the proximal end portion of the catheter assembly 302. The stent 304 has an inner surface, an outer surface, and is configured from multiple turns of an undulating element 305. The undulating element 305 may be configured in a ring or helical pattern.

The stent 304 has a proximal end portion 306 and distal end portion 308. The distal end portion 308 is formed into a branch having a first leg 310 and a second leg 312.

A graft 314 is arranged about the stent 104.

In one preferred embodiment, the stent 304 and graft 314 are constrained into a compacted delivery state by a first sheath 316 and second sheath 318. As shown in FIG. 3A, the first sheath 316 has been released allowing at least a portion of the stent 304 to expand as shown. The second sheath 318 is coupling the second leg 312 to the catheter assembly 302 as shown.

A tube 320 extends from a proximal end portion to a distal end portion of the catheter assembly 302. The tube 320 is positioned within and surrounded by the stent 304. The tube 320 is attached to the catheter assembly 302 and not attached to the stent 304 or graft 314. A movable element 322 having a first end 324 and second end 326 surrounds the stent 304 and graft 314. The first end 324 and second end 326 of the movable element 322 extend out a distal end portion of the tube 320. The movable element 322 is threaded through the tube from a distal end to a proximal end and is looped around the proximal end portion 306 of the stent 304 and graft 314. A further embodiment for "surrounding" the stent with the moveable element includes threading the moveable element 322 through the graft 314 or through the stent 304 as shown in FIG. 3B. As shown in FIG. 3B, the movable element 322 is capable of radially compressing at least a portion of the stent 304 as indicated by arrows 328 when tension is applied to the movable element ends 324 and 326. Additional movable elements may be added similar to those configurations described in FIGS. 1D and 2D.

Figure 3C:
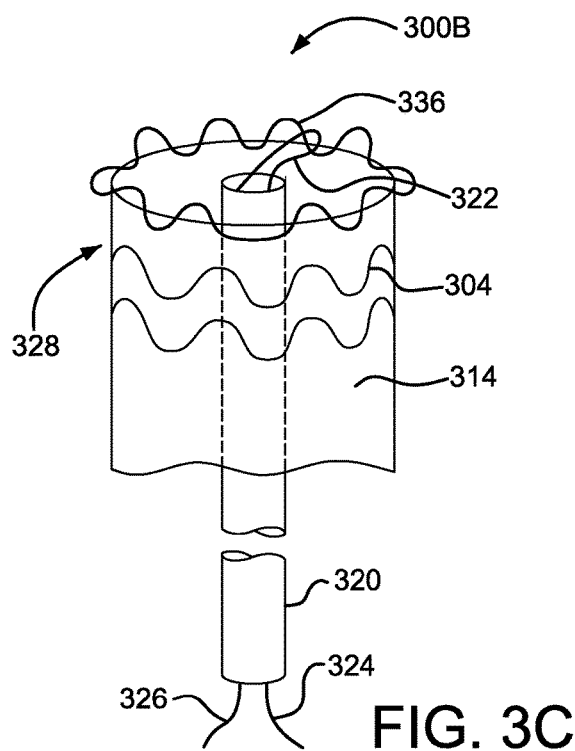
FIG. 3C is an enlarged simplified view of a medical apparatus according to an embodiment of the invention.

FIG. 3C is an enlarged simplified view of a portion of a medical apparatus according to an embodiment of the invention. As shown in FIG. 3C, second movable element 336 is in communication with first movable element 322. The second movable element 336 surrounds the stent member 304 and the first movable element 322 is looped through the second movable element 336. The second movable element 336 may also be threaded through the graft 314 or threaded through the stent 304 as shown in FIG. 3C.

The first end 324 and second end 326 of the first movable element 322 extend out a distal end portion of the tube 320. For example, the first movable element 322 is threaded through the tube from a distal end to a proximal end and is looped through the second movable element 336.

As shown in FIG. 3C, when tension is applied to the two ends 324 and 326 of the first movable element 322, the first movable element 322 pulls on the second movable element 336, radially compressing at least a portion of the stent 304 as indicated by arrows 328. Additional movable elements may be added similar to those configurations described in FIGS. 1D and 2D.

Figure 4A:
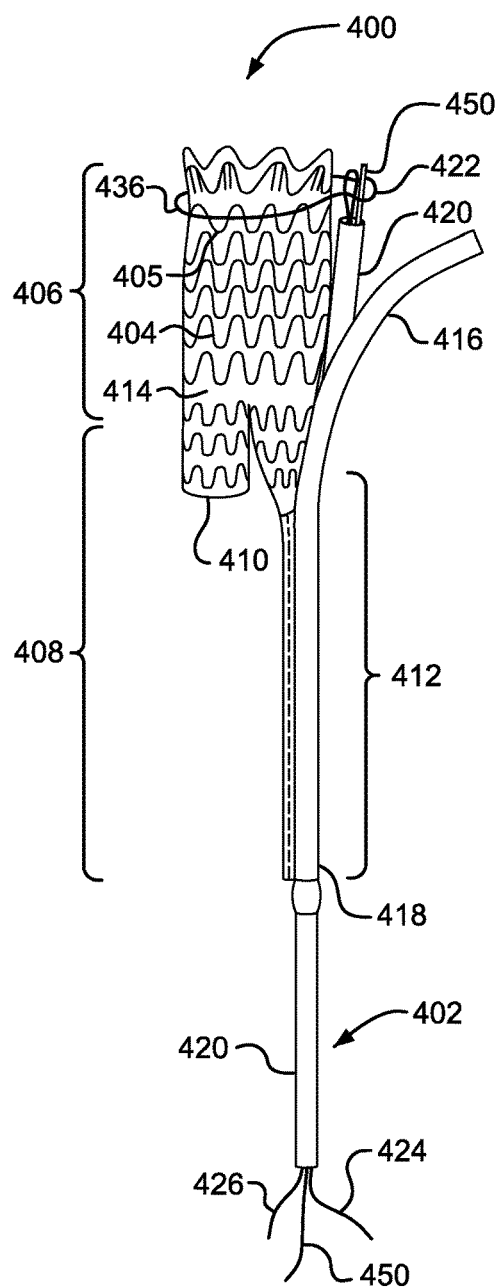
FIG. 4A is a medical apparatus according to an embodiment of the invention.
Figure 4B:
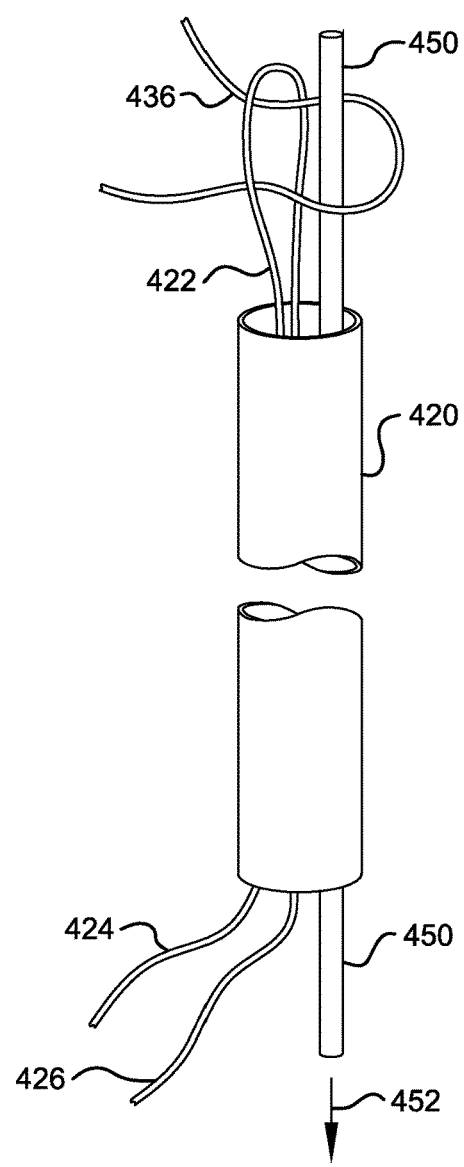
FIG. 4B is an enlarged simplified view of a medical apparatus according to an embodiment of the invention.

FIG. 4A is a medical apparatus according to an embodiment of the invention. FIG. 4B is an enlarged simplified view of a portion of the the medical apparatus shown in FIG. 4A.

Referring to FIGS. 4A and 4B, the medical apparatus is generally depicted by reference numeral 400. The medical apparatus 400 includes a catheter assembly 402, and stent 404 arranged on the proximal end portion of the catheter assembly 402. The stent 404 has an inner surface, an outer surface, and is configured from multiple turns of an undulating element 405. The undulating element 405 may be configured in a ring or helical pattern.

The stent 404 has a proximal end portion 406 and distal end portion 408. The distal end portion 408 is formed into a branch having a first leg 410 and a second leg 412.

A graft 414 is arranged about the stent 404.

The stent 404 and graft 414 are constrained into a compacted delivery state by a first sheath 416 and second sheath 418. As shown in FIG. 4A, the first sheath 416 has been released allowing at least a portion of the stent 404 to expand as shown. The second sheath 418 is coupling the second leg 412 to the catheter assembly 402 as shown.

A tube 420 extends from a proximal end portion to a distal end portion of the catheter assembly 402. The tube 420 is positioned adjacent the outer surface of the stent 404 and graft 414. The tube 420 is attached to the catheter assembly 402 and not attached to the stent 404 or graft 414. A second movable element 436 is in communication with a first movable element 422. The second movable element 436 surrounds the stent 404. The second movable element 436 is looped through the first movable element 422. A release pin 450 is threaded through the second movable element 436, thereby releasably attaching the second movable element 436 to the first movable element 422.

The first end 424 and second end 426 of the first movable element 422 extend out a distal end portion of the tube 420 along with the distal end of the release pin 450.

As shown in FIG. 4B, when tension is applied to the two ends 424 and 426 of the first movable element 422, the first movable element 422 pulls on the second movable element 436, radially compressing at least a portion of the stent as previously shown, for example, in FIG. 2B.

The release pin 450 can be translated in a distal direction as shown by direction arrow 452, thereby releasing the second movable element 436 from the first movable element 422.

FIG. 5A is a medical apparatus according to an embodiment of the invention. FIG. 5B is an enlarged simplified view of a portion of the medical apparatus shown in FIG. 5A.

Referring to FIGS. 5A and 5B, the medical apparatus is generally depicted as reference numeral 500. The medical apparatus 500 includes a catheter assembly 502, and stent 504 arranged on the proximal end portion of the catheter assembly 502. The stent 504 has an inner surface, an outer surface, and is configured from multiple turns of an undulating element 505. The undulating element 505 may be configured in a ring or helical pattern.

The stent 504 has a proximal end portion 506 and distal end portion 508. The distal end portion 508 is formed into a branch having a first leg 510 and a second leg 512.

A graft 514 is arranged about the stent 504.

In a preferred embodiment, the stent 504 and graft 514 are constrained into a compacted delivery state by a first sheath 516 and second sheath 518. As shown in FIG. 5A, the first sheath 516 has been released allowing at least a portion of the stent 504 to expand as shown. The second sheath 518 is coupling the second leg 512 to the catheter assembly 502 as shown.

A tube 520 extends from a proximal end portion to a distal end portion of the catheter assembly 502. The tube 520 is positioned adjacent the outer surface of the stent 504 and graft 514. The tube 520 is attached to the catheter assembly 502 and not attached to the stent 504 or graft 514.

A movable element 522 is threaded through the tube 520 and is circumferentially arranged around the stent 504. The movable element 522 is looped over release pin 550, thereby releasably attaching the movable element 522 to the release pin 550.

As shown in FIG. 5B, when tension is applied to the two ends 524 and 526 of the movable element, the movable element 522 radially compresses at least a portion of the stent as previously shown, for example, in FIG. 2B. When desired, the release pin 550 can be translated in a distal direction as shown by direction arrow 552, thereby releasing the movable element 522 from the release pin 550 allowing the movable element 522 to be withdrawn.

FIG. 6A is a medical apparatus according to an embodiment of the invention. FIG. 6B is an enlarged simplified view of a portion of the medical apparatus shown in FIG. 6A.

Referring to FIGS. 6A and 6B, the medical apparatus is generally depicted as reference numeral 600. The medical apparatus 600 includes a catheter assembly 602, and stent 604 arranged on the proximal end portion of the catheter assembly 602. The stent 604 has an inner surface, an outer surface, and is configured from multiple turns of an undulating element 605. The undulating element 605 may be configured in a ring or helical pattern.

The stent 604 has a proximal end portion 606 and distal end portion 608. The distal end portion 608 is formed into a branch having a first leg 610 and a second leg 612.

A graft 614 is arranged about the stent 604. The stent 604 and graft 614 are constrained into a compacted delivery state (or first diameter) by a first sheath 616 and second sheath 618. As shown in FIG. 6A, the first sheath 616 has been released allowing at least a portion of the stent 604 to expand as shown. The second sheath 618 is coupling the second leg 612 to the catheter assembly 602 as shown.

After the release of the first sheath 616, the stent 604 is allowed to self expand into a second diameter that is greater than the initial compacted first diameter. The second diameter is defined by a secondary constraint 654. The secondary constraint 654 can be comprised, for example, of a flexible filament that encircles a proximal end portion 606 of the stent and graft. The secondary constraint 654 prevents further self expansion of the stent.

As shown in FIG. 6B, the secondary constraint 654 is looped around the stent (not shown) and is threaded through a first end of the secondary constraint 654. The second end of the secondary constraint 654 is looped onto a release pin 650. Once the apparatus 600 is properly positioned within a vessel target site, the secondary constraint 654 can be released by translating the release pin 650 in a distal direction as shown by direction arrow 652. By translating the release pin 650, the stent is released from the secondary constraint and thereby allowed to further expand into a third diameter that is greater than the second and first diameters.

Optionally, a retrieval cord or filament 656 can be used to join the secondary constraint 654 to the release pin 650. Therefore when the release pin is translated distally, the secondary constraint 654 is withdrawn along with the release pin 650.

Figure 7A:
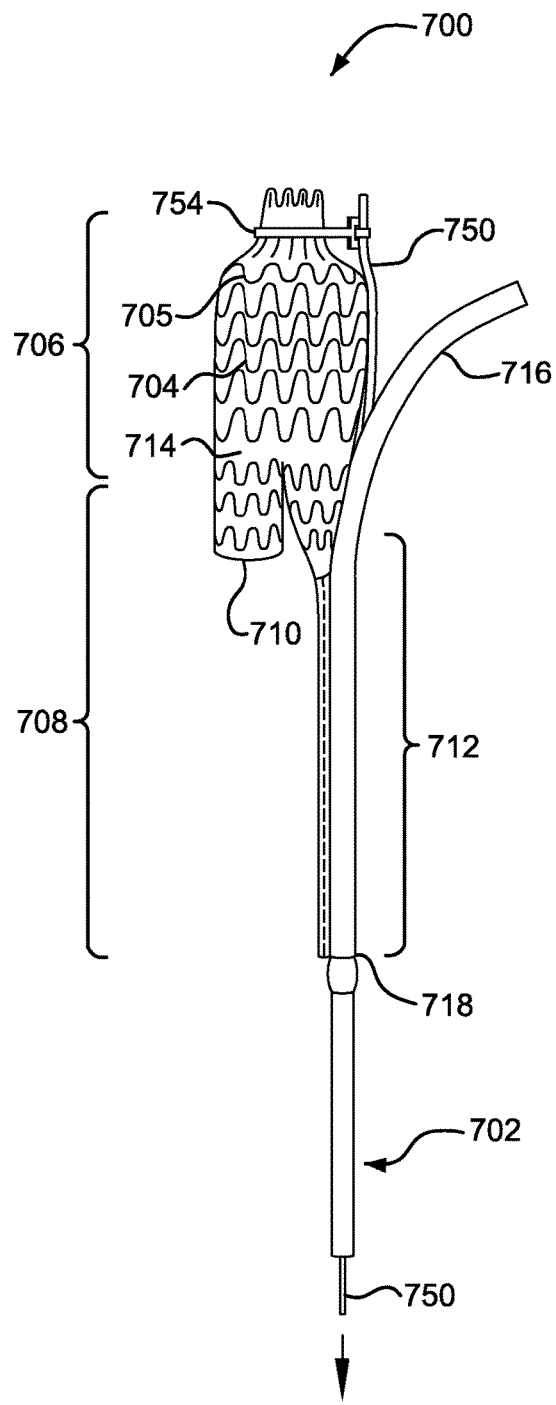
FIG. 7A is a medical apparatus according to an embodiment of the invention.
Figure 7B:
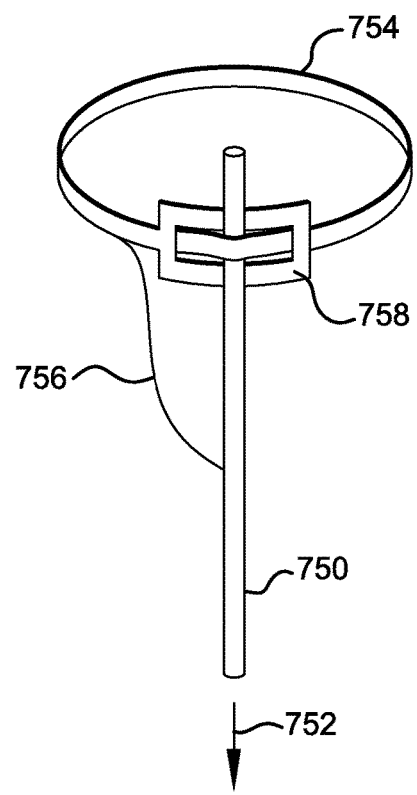
FIG. 7B is an enlarged simplified view of a medical apparatus according to an embodiment of the invention.

FIG. 7A is a medical apparatus according to an embodiment of the invention. FIG. 7B is an enlarged simplified view of a portion of the medical apparatus shown in FIG. 7A.

Referring to FIGS. 7A and 7B, the medical apparatus is generally depicted as reference numeral 700. The medical apparatus 700 includes a catheter assembly 702, and stent 704 arranged on the proximal end portion of the catheter assembly 702. The stent 704 has an inner surface, an outer surface, and is configured from multiple turns of an undulating element 705. The undulating element 705 may be configured in a ring or helical pattern.

The stent 704 has a proximal end portion 706 and distal end portion 708. The distal end portion 708 is formed into a branch having a first leg 710 and a second leg 712.

A graft 714 is arranged about the stent 704. The stent 704 and graft 714 are constrained into a compacted delivery state (or first diameter) by a first sheath 716 and second sheath 718. As shown in FIG. 7A, the first sheath 716 has been released allowing at least a portion of the stent 704 to expand as shown. The second sheath 718 is coupling the second leg 712 to the catheter assembly 702 as shown.

After the release of the first sheath 716, the stent 704 is allowed to self expand into a second diameter that is greater than the initial compacted first diameter. The second diameter is defined by a secondary constraint 754. The secondary constraint 754 is comprised of a flexible band that encircles a proximal end portion 706 of the stent graft. The secondary constraint prevents further self expansion of the stent graft.

As shown in FIG. 7B, the secondary constraint 754 is looped around the stent and is threaded through a latch 758 located near a first end of the secondary constraint 754. A release pin 750 is threaded through the latch 758 to prevent further expansion of the secondary constraint 754. Once the apparatus 700 is properly positioned within a vessel target site, the secondary constraint 754 can be released by translating the release pin 750 in a distal direction as shown by direction arrow 752. By translating the release pin 750, the stent 704 is released from the secondary constraint 754 and thereby allowed to further expand into a third diameter that is greater than the second and first diameters. Optionally, a retrieval cord or filament 756 can be used to join the secondary constraint 754 to the release pin 750. Therefore when the release pin is translated distally, the secondary constraint 754 is withdrawn along with the release pin 650.

Figure 8A:
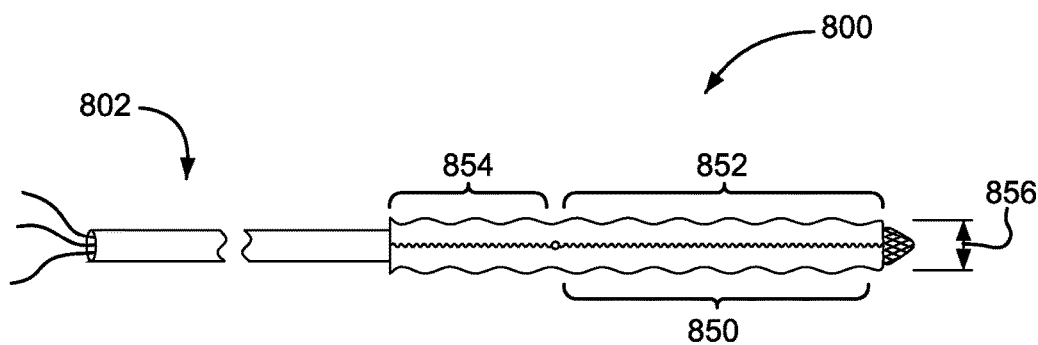
FIGS. 8A-8C is a medical apparatus according to an embodiment of the invention.
Figure 8B:
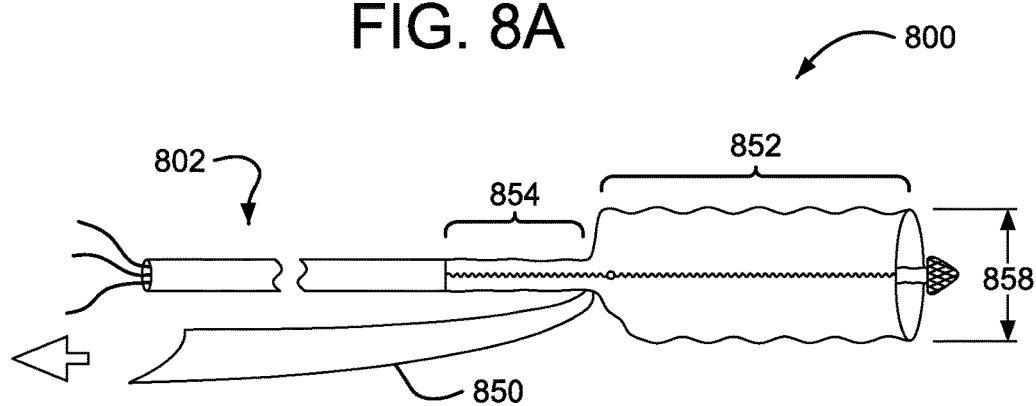
Figure 8C:
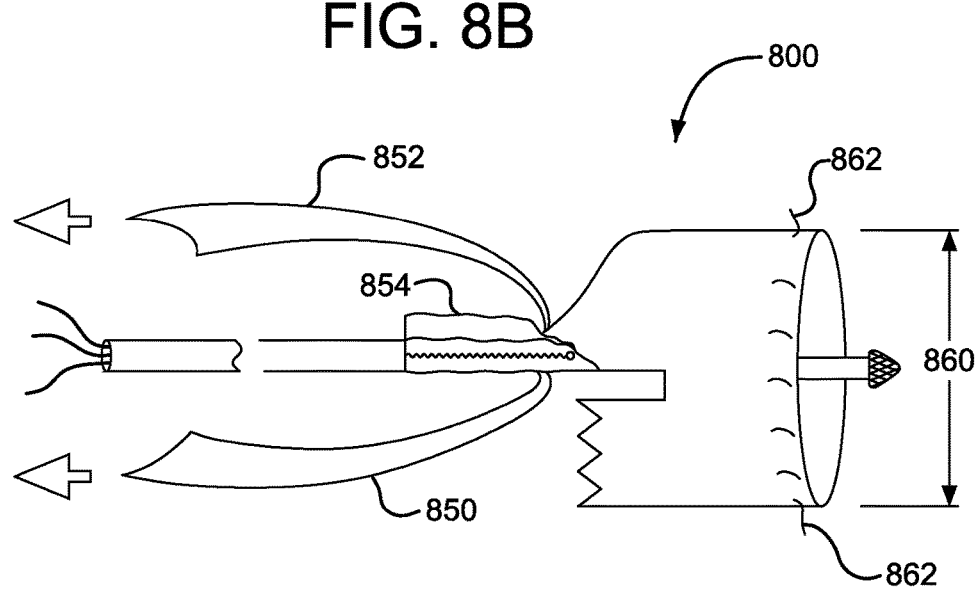

FIGS. 8A through 8C depict a medical apparatus according to an embodiment of the invention.

Referring to FIGS. 8A through 8C, the medical apparatus is generally depicted as reference numeral 800. The medical apparatus 800 includes a catheter assembly 802, and stent arranged on the proximal end portion of the catheter assembly 802. As shown in FIG. 8A the medical apparatus 800 has a stent constrained into a small delivery diameter 856. The stent is held in this small delivery diameter by constraining sheaths 850 and 854. The sheath 850 constrains the trunk of the stent while the sheath 854 constrains the extended leg portion of the stent. A third constraining sheath 852 is contained within the sheath 850.

Referring to FIG. 8B, when the medical apparatus 800 is positioned within a target site, the sheath 850 can be released, allowing at least a portion of the stent to expand to a diameter 858 that is larger than the initial small delivery diameter 856. The sheath 852 therefore constrains the stent 804 to an intermediate diameter. The sheath 854 constrains the extended leg portion of the stent onto the catheter assembly 802, thereby allowing the medical apparatus to be repositioned, rotated or precisely aligned to the target site. As shown in FIG. 8C, when the medical apparatus is precisely positioned, the sheath 852 can be released, allowing the stent to fully expand to a large deployed diameter 860. The deployed diameter 860 is larger than the intermediate diameter 858. The intermediate diameter 858 is larger than the delivery diameter 856 as shown in FIGS. 8A through 8C. Stent anchoring barbs or hooks 862 (when provided) are therefore constrained to the intermediate diameter 858 during final manipulation and positioning of the medical apparatus and allowed to expand and engage a vessel when the constraining sheath 852 is released.

FIG. 9A is a partial side view of a medical apparatus 900, having a constrained medical device 960 located near or at the distal end of a catheter assembly 962. The catheter assembly 962 has a catheter shaft 964 and a distal guidewire port 966. FIG. 9B is a cross-sectional view of the catheter shaft 964. Shown contained within the catheter shaft 964 is a guidewire 970, a release member 972 and an adjustment member 974. The release member can be a cord, thread, wire, pin, tube or other element used to release a stent (or other medical device) from a constraint, thereby allowing the device to expand from a first compacted delivery profile to a second larger profile. The adjustment member can be a cord, thread, wire, pin, tube or other element used to alter the second profile of at least a portion of the medical device. A catheter used to deliver a medical apparatus can have one, two, three, four or five or more release members combined with one, two, three, four or five or more adjustment members. The release members and adjustment members can be contained in separate or shared lumens within the catheter shaft 964.

FIGS. 10A and 10B show generalized views of a medical apparatus according to an embodiment of the invention (previously described in FIGS. 2A and 2B). Shown in FIG. 10A is a medical apparatus 1000, comprised of a stent 1002 having anchor barbs or hooks 1004. Shown is a tube 1006 having a first movable element 1008 located therein. The first movable element 1008 is shown looped through a second movable element 1010. As shown in FIG. 10B, when tension 1012 is applied to the ends of the first movable element 1008, the second movable element 1010 is drawn into the tube 1006. When the second movable element 1010 is drawn into the tube 1006, the stent graft is compressed in the direction indicated by arrows 1014. The anchors or barbs 1004 are therefore retracted and pulled inwardly away from a vessel wall. The retraction of the anchors or barbs will allow the medical apparatus 1000 to be longitudinally and/or rotationally adjusted. When in the precise target area the tension 1012 on the movable element can be removed, allowing the stent to self expand and engage the anchors or barbs into a vessel wall.

Figure 10C:
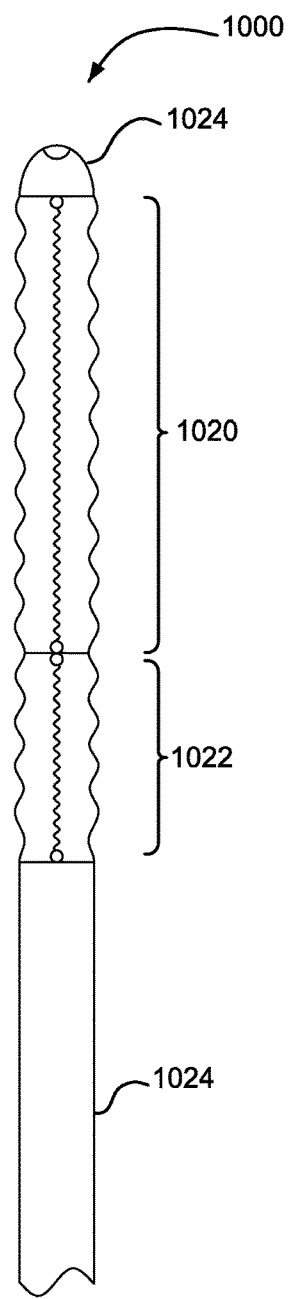
Figure 10D:
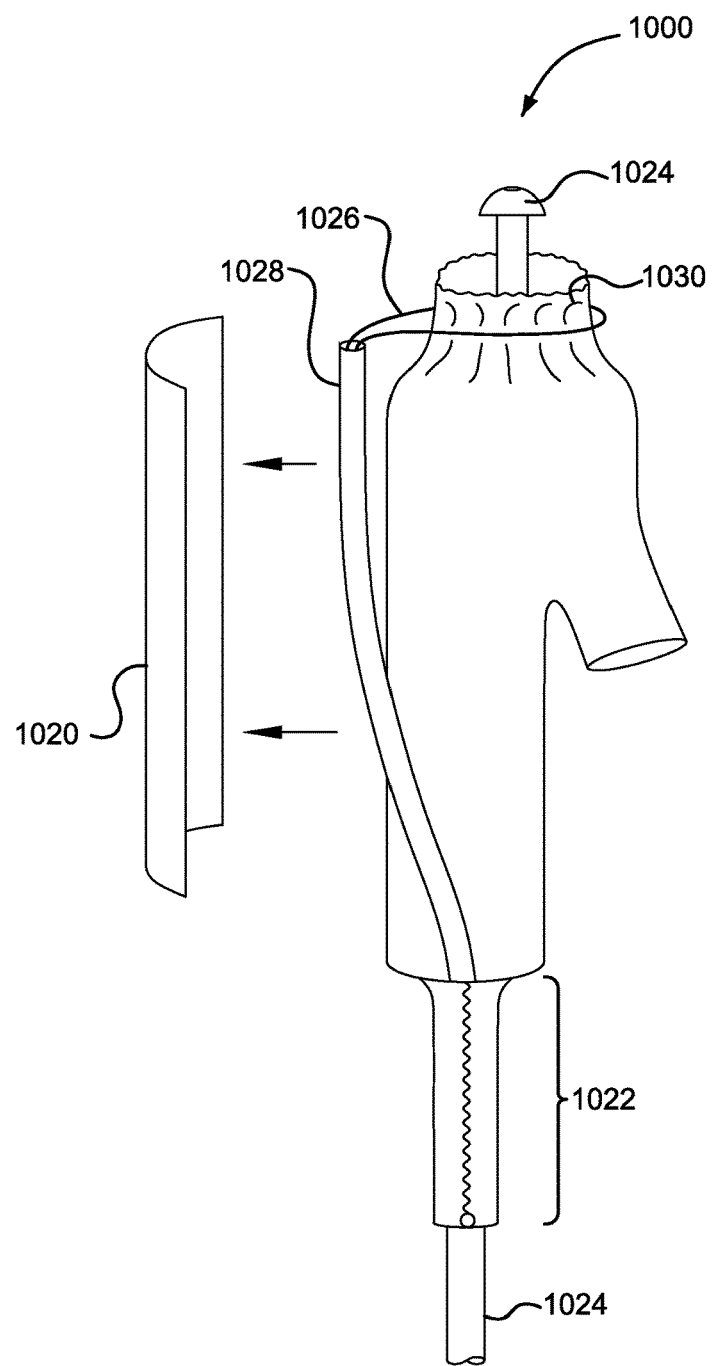

FIGS. 10C through 10H show a generalized delivery sequence according to an embodiment of the invention. Shown in FIG. 10C is a medical apparatus 1000, having a first constraining sheath 1020, a second constraining sheath 1022 and a catheter assembly 1024. Constrained and contained within the first and second sheaths 1020, 1022 is a bifurcated stent having a trunk, a first short leg and a second long leg. As shown in FIG. 10D, when the medical apparatus is positioned at a target site, the first constraining sheath 1020 is released allowing a portion of the stent and first short leg to self expand. A portion of the stent is held in a constrained small diameter state by movable element 1026. The movable element 1026 is located in tube 1028. The stent anchors or barbs 1030 are constrained and pulled inwardly by the movable element 1026, so that the anchors or barbs do not engage a vessel wall. The second constraining sheath 1022 compresses the stent graft second long leg onto the catheter assembly 1024. Thus the medical apparatus is captured by the catheter assembly, allowing subsequent repositioning of the medical apparatus.

Figure 10E:
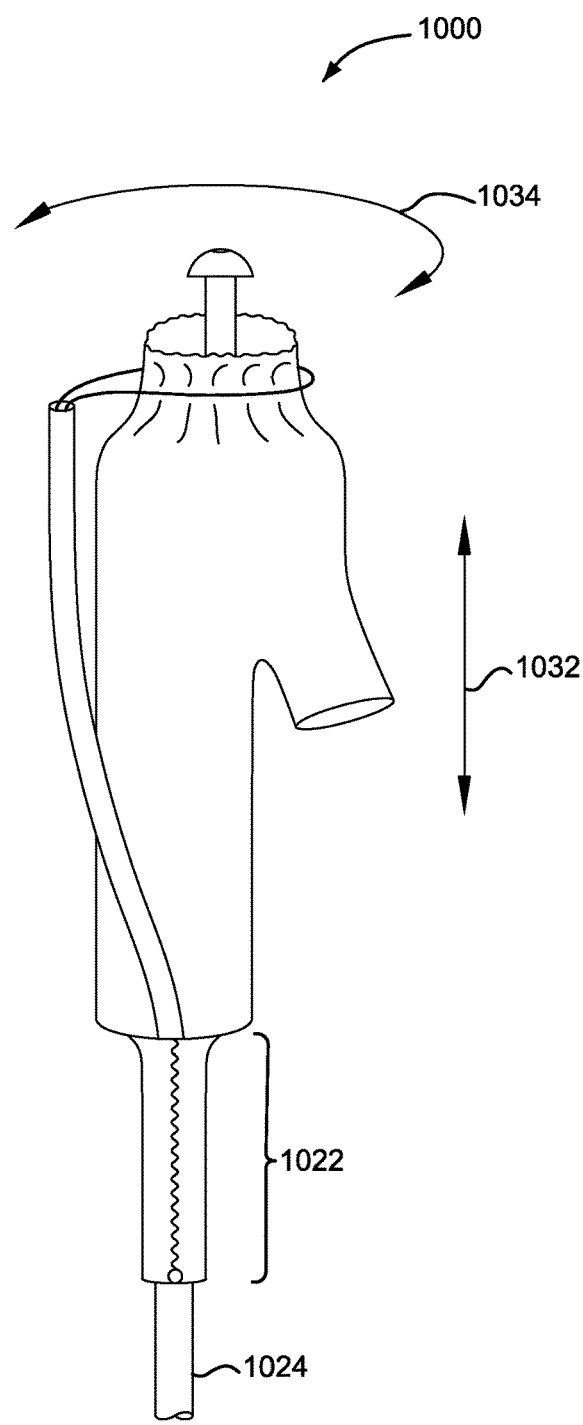

As shown in FIG. 10E, the medical apparatus 1000 can now be readjusted in the longitudinal direction 1032 and/or in the angular direction 1034 through manipulations of the catheter assembly 1024.

Figure 10F:
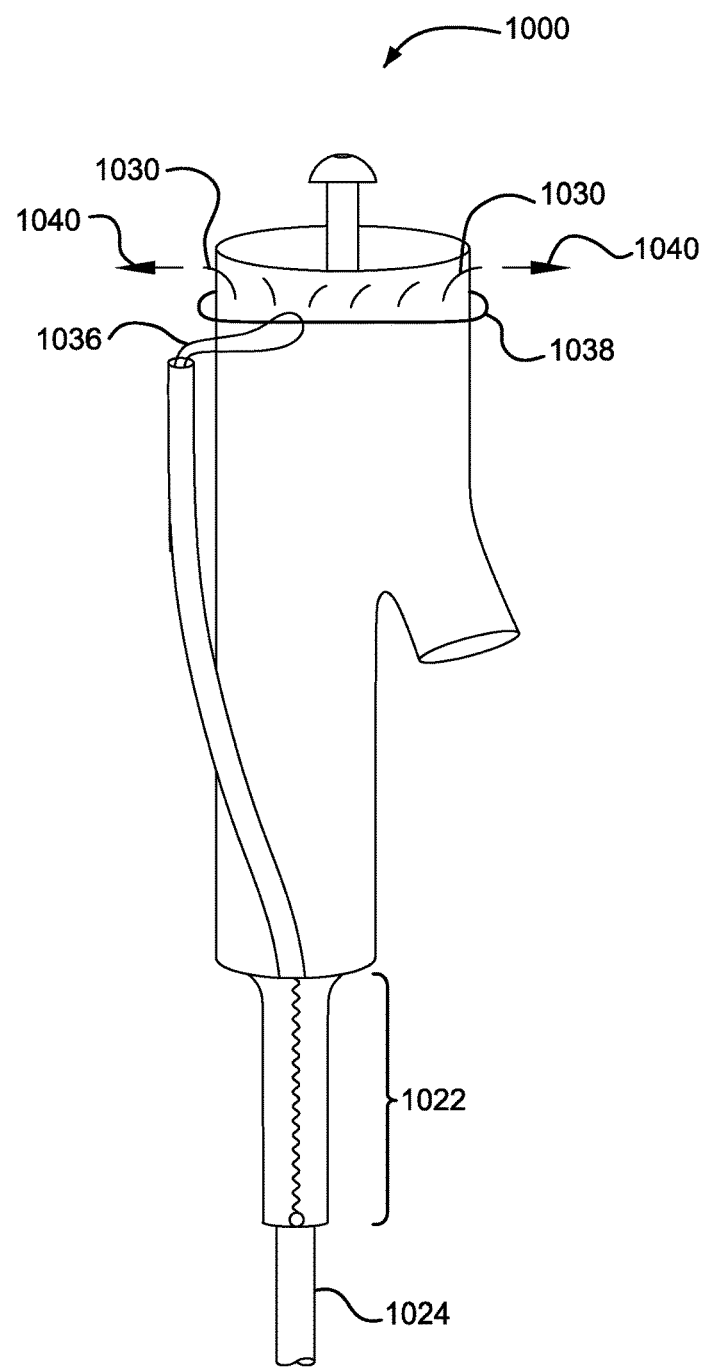

As shown in FIG. 10F, when the medical apparatus is precisely positioned, tension on first movable element 1036 is relaxed, allowing second movable element 1038 to expand. As second movable element 1038 expands, the stent is allowed to further expand in the direction 1040, engaging the anchors or barbs 1030 into a vessel wall.

Figure 10G:
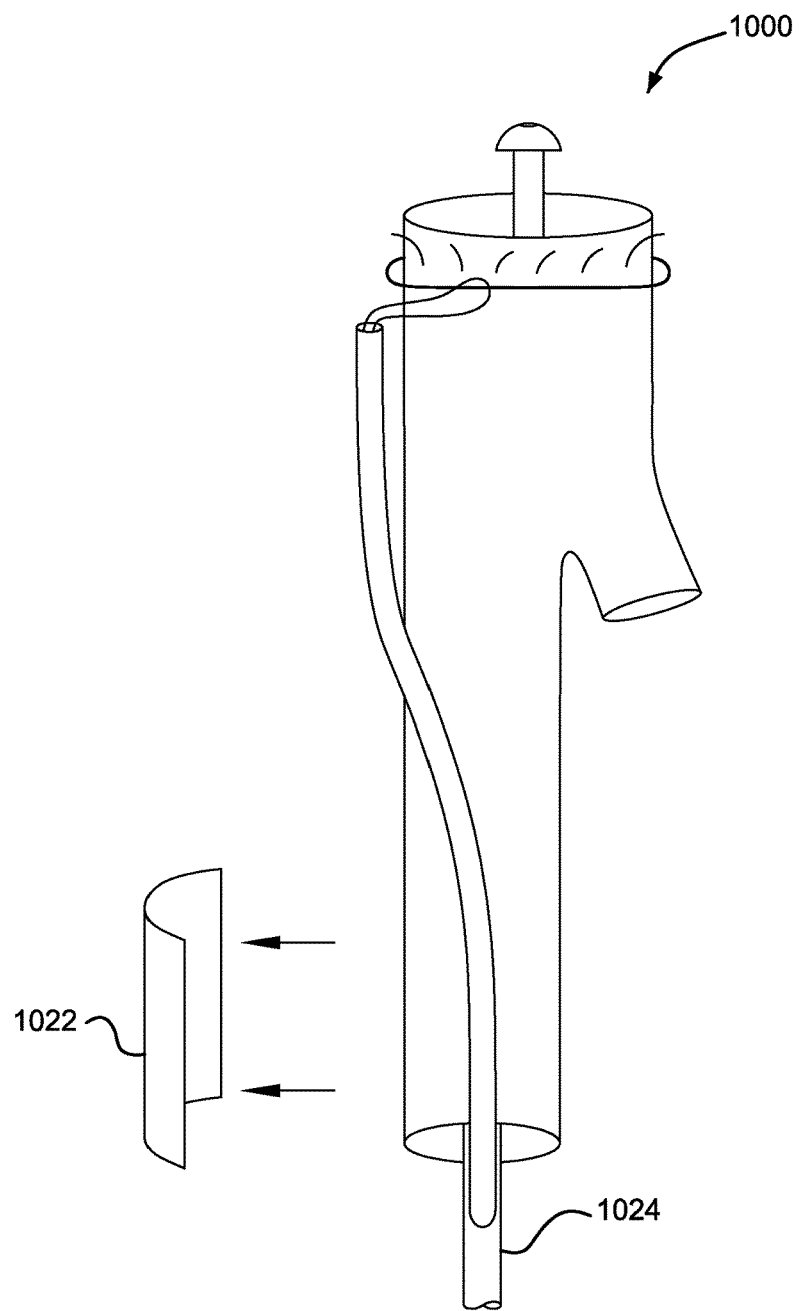

As shown in FIG. 10G, the second constraining sheath 1022 can be released, allowing the second long leg to self expand.

Figure 10H:
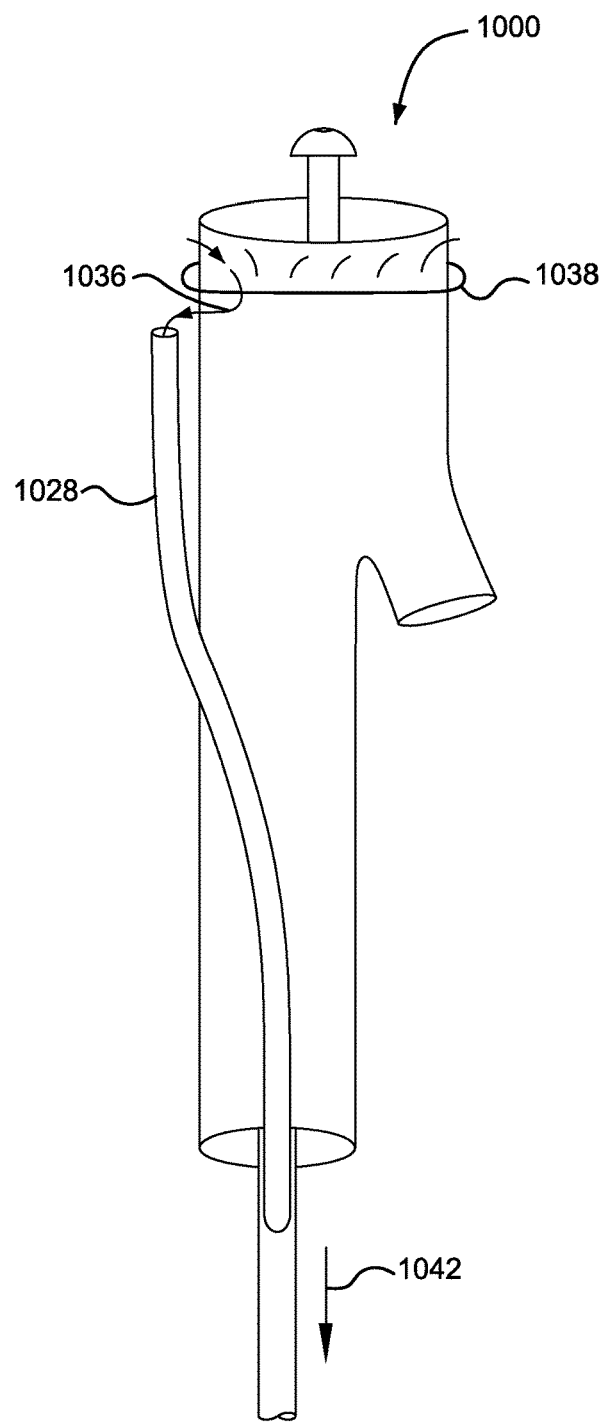

As shown in FIG. 10H, one end of first movable element 1036 can be tensioned, allowing first movable element 1036 to be un-looped from second movable element 1038. First movable element 1036 can then be withdrawn through the tube 1028. The expanded stent graft is now unattached from the catheter assembly, allowing withdrawal 1042 of the catheter assembly.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. An apparatus, comprising:
a catheter having a proximal end portion and distal end portion and defining a lumen;
a stent having a stent inner surface, a stent outer surface, and a stent lumen defined by the stent inner surface, the proximal end of the catheter being positioned inside of the stent lumen;
a graft member arranged about the stent, the stent and the graft forming a bifurcated medical device having a trunk and legs;
a sheath configured to constrain the stent and graft in a delivery diameter and to release which causes a portion of the stent and graft to expand to an intermediate diameter that is larger than the delivery diameter; and
a movable element threaded through the graft member such that a first end and a second end of the movable element extend circumferentially about the stent in opposing directions and extend through the distal end portion of the catheter such that the first and second ends are tensionable, the movable element defining the intermediate diameter to which the portion of the stent and graft expand to upon release of the sheath,
wherein the movable element is movable between a first direction to radially compress the portion of the stent from the intermediate diameter and a second direction opposite the first direction to allow expansion of the portion of the stent from the intermediate diameter to a deployed diameter of the stent, the movable element being separable from the graft member to allow withdrawal of the movable element after deployment of the stent and graft member.

2. The apparatus of claim 1, wherein the movable element is an elongated element that extends through and exits the lumen of the catheter at the distal end portion of the catheter.

3. The apparatus of claim 1, wherein the movable element comprises a filament.

4. The apparatus of claim 3, wherein the filament comprises a wire.

5. The apparatus of claim 3, wherein the filament comprises a polymer.

6. The apparatus of claim 5, wherein the polymer comprises a fluoropolymer.

7. The apparatus of claim 6, wherein the fluoropolymer comprises polytetrafluoroethylene.

8. The apparatus of claim 7, wherein the polytetrafluoroethylene comprises expanded polytetrafluoroethylene.

9. The apparatus of claim 1, wherein the graft member is positioned on the stent inner surface of the stent.

10. The apparatus of claim 1, wherein the proximal end of the catheter is positioned on the stent inner surface of the stent.

11. The apparatus of claim 1, wherein the stent is incorporated into an internal wall structure of the graft member.

12. The apparatus of claim 1, wherein the graft member is positioned on the stent outer surface.

13. An apparatus, comprising:
a catheter having a proximal end portion and distal end portion;
a bifurcated stent having a trunk with a stent inner surface, a stent outer surface, and a stent lumen defined by the stent inner surface, the proximal end of the catheter being positioned adjacent the stent outer surface and outside of the stent lumen;

a sheath configured to constrain the stent in a delivery diameter and to release which causes at least a portion of the stent to expand to an intermediate diameter that is larger than the delivery diameter; and a movable element extending about the stent outer surface such that a first end and a second end of the movable element extend circumferentially about the stent in opposing directions and extend through the distal end portion of the catheter such that the first and second ends are tensionable, the movable element defining the intermediate diameter to which the stent expands to upon release of the sheath, wherein the movable element is movable between a first direction to radially compress at least a portion of the stent from the intermediate diameter and a second direction opposite the first direction to allow radial expansion of the at least a portion of the stent from the intermediate diameter to a deployed diameter of the stent, the movable element being separable from the stent to allow withdrawal of the movable element after deployment of the stent.

14. The apparatus of claim 13, further comprising a graft member arranged about at least a portion of the stent.

15. The apparatus of claim 14, wherein the movable element is an elongated element that extends through and exits the lumen of the catheter at the distal end portion of the catheter.

16. The apparatus of claim 14, wherein the movable element is arranged circumferentially around the stent and threaded through the graft member and not through the stent.

17. The apparatus of claim 14, wherein the movable element is threaded through the graft member and not through the stent.

18. The apparatus of claim 14, wherein the stent is incorporated into an internal wall structure of the graft.

19. The apparatus of claim 14, wherein the movable element comprises a filament.

20. The apparatus of claim 19, wherein the filament comprises a wire.

21. The apparatus of claim 19, wherein the filament comprises a polymer.

22. The apparatus of claim 21, wherein the polymer comprises a fluoropolymer.

23. The apparatus of claim 22, wherein the fluoropolymer comprises polytetrafluoroethylene.

24. The apparatus of claim 23, wherein the polytetrafluoroethylene comprises expanded polytetrafluoroethylene.

25. The apparatus of claim 19, wherein the filament is arranged circumferentially around the graft member and is threaded between adjacent undulations of the stent.

26. The apparatus of claim 14, wherein the graft member is positioned on the stent inner surface.

27. The apparatus of claim 14, wherein the graft member is positioned on the stent outer surface.

28. An apparatus, comprising:

a catheter having a proximal end portion and distal end portion and defining a lumen;

a stent having a stent inner surface, a stent outer surface, and a stent lumen defined by the stent inner surface, the proximal end of the catheter being positioned inside of the stent lumen;

a graft member arranged about the stent;

a sheath configured to constrain the stent and graft in a delivery diameter and to release which causes a portion of the stent and graft to expand to an intermediate diameter that is larger than the delivery diameter; and a movable element threaded through the graft member such that a first end and a second end of the movable element extend circumferentially about the stent in opposing directions and extend through the distal end portion of the catheter such that the first and second ends are tensionable, the movable element defining the intermediate diameter to which the portion of the stent and graft expand to upon release of the sheath, wherein the movable element is movable between a first direction to radially compress the portion of the stent from the intermediate diameter and a second direction opposite the first direction to allow expansion of the portion of the stent from the intermediate diameter to a deployed diameter of the stent, the movable element being separable from the graft member to allow withdrawal of the movable element after deployment of the stent and graft member.

* * * * *